US006848462B2

(12) United States Patent
Covington et al.

(10) Patent No.: US 6,848,462 B2
(45) Date of Patent: Feb. 1, 2005

(54) ADHESIVELESS MICROFLUIDIC DEVICE FABRICATION

(75) Inventors: Joseph F. Covington, San Gabriel, CA (US); Steven E. Hobbs, West Hills, CA (US); Jeffrey A. Koehler, Pasadena, CA (US); Paren P. Patel, Sierra Madre, CA (US); Marci Pezzuto, Pasadena, CA (US); Mark S. Scheib, La Verne, CA (US)

(73) Assignee: Nanostream, Inc., Pasadena, CA (US)

( * ) Notice: Subject to any disclaimer, the term of this patent is extended or adjusted under 35 U.S.C. 154(b) by 238 days.

(21) Appl. No.: 10/313,231

(22) Filed: Dec. 6, 2002

(65) Prior Publication Data

US 2003/0106799 A1 Jun. 12, 2003

Related U.S. Application Data

(60) Provisional application No. 60/393,953, filed on Jul. 2, 2002, and provisional application No. 60/338,286, filed on Dec. 6, 2001.

(51) Int. Cl.[7] .................................................. F15C 1/06
(52) U.S. Cl. ............................ 137/15.01; 137/315.01; 137/833; 251/368; 204/601; 422/100
(58) Field of Search .................... 137/15.01, 315.01, 137/833; 251/368; 422/100; 204/601

(56) References Cited

U.S. PATENT DOCUMENTS

| | | | | |
|---|---|---|---|---|
| 3,680,576 A | * | 8/1972 | Kiwak ......................... 137/833 |
| 3,798,727 A | * | 3/1974 | Brock ...................... 29/890.09 |
| 4,558,333 A | | 12/1985 | Sugitani et al. |
| 5,041,181 A | | 8/1991 | Brackett et al. ............... 156/84 |
| 5,070,606 A | | 12/1991 | Hoopman et al. ........ 29/890.03 |
| 5,376,252 A | | 12/1994 | Ekström et al. |
| 5,443,890 A | | 8/1995 | Öhman ........................ 428/167 |
| 5,478,751 A | | 12/1995 | Oosta et al. ................. 436/165 |
| 5,525,405 A | | 6/1996 | Coverdell et al. ........... 428/213 |
| 5,690,763 A | | 11/1997 | Ashmead et al. .............. 156/60 |
| 5,792,943 A | | 8/1998 | Craig ......................... 73/61.52 |
| 5,846,396 A | | 12/1998 | Zanzucchi et al. ........... 204/601 |

(List continued on next page.)

FOREIGN PATENT DOCUMENTS

| | | | |
|---|---|---|---|
| EP | 0 708 331 A1 | 4/1996 | ......... G01N/27/447 |
| EP | 1 106 244 A2 | 6/2001 | |
| WO | WO 97/06468 | 2/1997 | |

(List continued on next page.)

OTHER PUBLICATIONS

Vela, A., "An Approach for the Thermal Bonding of Micro–Fluidic Devices," Institute for Systems Research, UG 2001–8.

(List continued on next page.)

*Primary Examiner*—A. Michael Chambers
(74) *Attorney, Agent, or Firm*—Vincent K. Gustafson; Michael F. Labbee

(57) ABSTRACT

A method for fabricating a microfluidic device where first and second substantially flat platens are provided. Multiple substantially planar, substantially metal-free, adhesiveless polymer device layers, the device layers including a first cover layer, second cover layer, and at least one stencil layer defining a microfluidic channel penetrating through the entire thickness of the stencil layer also are provided. Each stencil layer is disposed between other device layers such that the channel is bounded laterally by a stencil layer, and bounded from above and below by surrounding device layers to define an upper channel surface and a lower channel surface. The device layers are stacked between the first platen and the second platen. The stacked device layers are controllably heated according to a heating profile adapted to form a substantially sealed adhesiveless microfluidic device wherein each upper channel surface remains distinct from its corresponding lower channel surface. The resulting microfluidic device has high inter-layer bond strength while preserving the integrity of the channel(s) defined in the stencil layer(s).

62 Claims, 19 Drawing Sheets

U.S. PATENT DOCUMENTS

| | | | |
|---|---|---|---|
| 5,882,465 A | 3/1999 | McReynolds | 156/285 |
| 5,885,470 A | 3/1999 | Parce et al. | 216/33 |
| 5,935,401 A | 8/1999 | Amigo | 204/454 |
| 6,010,607 A | 1/2000 | Ramsey | 204/435 |
| 6,033,546 A | 3/2000 | Ramsey | 204/603 |
| 6,043,080 A | 3/2000 | Lipshutz et al. | 435/287.2 |
| 6,048,498 A | 4/2000 | Kennedy | 422/99 |
| 6,068,751 A | 5/2000 | Neukermans et al. | 204/601 |
| 6,073,482 A | 6/2000 | Moles | 73/53.01 |
| 6,074,725 A | 6/2000 | Kennedy | 428/188 |
| 6,149,870 A | 11/2000 | Parce et al. | 422/100 |
| 6,150,180 A | 11/2000 | Parce et al. | 436/514 |
| 6,156,438 A | 12/2000 | Gumm et al. | 428/458 |
| 6,240,790 B1 | 6/2001 | Swedberg et al. | |
| 6,312,888 B1 | 11/2001 | Wong et al. | 435/4 |
| 6,352,577 B1 | 3/2002 | Martin et al. | 96/4 |
| 6,408,878 B2 | 6/2002 | Unger et al. | 137/597 |
| 6,428,896 B1 | 8/2002 | Ramsey et al. | 428/428 |
| 6,494,614 B1 | 12/2002 | Bennett et al. | 366/336 |
| 6,514,399 B1 | 2/2003 | Parce et al. | 204/600 |
| 6,536,477 B1 * | 3/2003 | O'Connor et al. | 137/833 |
| 6,537,506 B1 | 3/2003 | Schwalbe et al. | 422/130 |
| 6,623,860 B2 | 9/2003 | Hu et al. | 428/411.1 |
| 6,676,835 B2 * | 1/2004 | O'Connor et al. | 210/542 |
| 6,685,841 B2 * | 2/2004 | Lopez et al. | 210/767 |
| 6,729,352 B2 * | 5/2004 | O'Connor et al. | 137/827 |
| 6,769,444 B2 * | 8/2004 | Guzman et al. | 137/15.01 |
| 2002/0094533 A1 | 7/2002 | Hess et al. | 435/6 |
| 2002/0124896 A1 * | 9/2002 | O'Connor et al. | 137/833 |
| 2002/0189947 A1 | 12/2002 | Paul et al. | 204/461 |
| 2002/0199094 A1 | 12/2002 | Strand et al. | 713/150 |
| 2003/0180711 A1 | 9/2003 | Turner et al. | 435/4 |

FOREIGN PATENT DOCUMENTS

| | | | |
|---|---|---|---|
| WO | WO 98/07069 | 2/1998 | |
| WO | WO 98/45693 | 10/1998 | G01N/27/26 |
| WO | WO 99/19717 | 4/1999 | G01N/25/22 |
| WO | WO 99/56954 | 11/1999 | B32B/31/26 |
| WO | WO 99/60397 | 11/1999 | G01N/33/483 |
| WO | WO 00/21659 | 4/2000 | |
| WO | WO 01/01025 | 1/2001 | F16K/17/00 |
| WO | WO 01/09598 A1 | 2/2001 | |
| WO | WO 01/38865 A1 | 5/2001 | |
| WO | WO 02/28532 | 4/2002 | B01L/3/00 |

OTHER PUBLICATIONS

Grodzinski, P., "*Development of Plastic Microfluidic Devices for Sample Preparation,*" Presentation from BioMEMS 2000, Columbus, Ohio, Sep. 24, 2000.

Nguyentat, T., "*Diffusion Bonding —An Advanced Material Process for Aerospace Technology,*" http://www.vacets.org/vtic07/ttnguyen.htm.

Jacobson, S. et al, "*Integrated Microdevice for DNA Restriction Fragment Analysis,*" Anal. Chem. 1996, 68, 720–723.

Moles, D., "*Microanalytical Systems Development at YSI: A Non–Silicon Approach,*" Presentation from BioMEMS & Biomedical Nanotechnology World 2000 Conference, Sep. 23–26, 2000.

Metz, S. et al., "*Polyimide–based Microfluidic Devices,*" Lab on a Chip, 2001, 1, 29–34.

Soper, S. et al., "*Polymetric Microelectromechanical Systems,*" Anl. Chem., Oct. 1, 2000; pp. 643 A–651 A.

Olsen, Kimberly G., et al., *Immobilization of DNA Hydrogel Plugs in Microfluidic Channels*, "Analytical Chemistry," vol. 74, No. 6, Mar. 15, 2002, pp. 1436–1441.

Martin, Peter M., et al., "Laminated Ceramic Microfluidic Components for Microreactor Applications," Web document published at: www.pnl.gov/microcats/aboutus/publications/microfabrication/laminceramic–rev.pdf.

Kameoka, Jun, et al., *A Polymeric Microfluidic Chip for CE/MS Determination of Small Molecules*, "Analytical Chemistry," vol. 73, No. 9, May 1, 2001, pp. 1935–1941.

Fan, Z.H., et al., "Plastic Microfluidic Devices for DNA Sequencing and Protein Separation," *Micro Total Analysis Systems*, J.M. Ramsey and A, van den Berg (eds.), 2001, Kluwer Academic Publishers, The Netherlands, pp. 19–21.

Liu, Yingjie, et al., "Microfabricated Polycarbonate CE Devices for DNA Analysis," *Micro Total Analysis Systems*, J.M. Ramsey and A. van den Berg (eds.), 2001, Kluwer Academic Publishers, The Netherlands, pp. 119–120.

Palm, Anders, et al., "Integrated Sample Preparation and MALDI MS on a disc," *Micro Total Analysis Systems*, J.M. Ramsey and A. van den Berg (eds.), 2001, Kluwer Academic Publishers, The Netherlands, pp. 216–218.

Svedberg, Malin, et al., "Electrospray From A Plastic Chip," *Micro Total Analysis Systems*, J.M. Ramsey and A. van den Berg (eds.), 2001, Kluwer Academic Publishers, The Netherlands, pp. 335–336.

Prins, M.W.J., et al., *Multichannel structures made from micrometre–thick plastic foils*, "J. Micromech. Microeng.," 1999, vol. 9, pp. 362–363.

Martin, P.M., et al., *Fabrication of plastic microfluidic components*, "Microfluidic Devices and Systems," Sep. 21–22 1998, Santa Clara, California, SPIE—The International Society for Optical Engineering, vol. 3515, pp. 172–176.

Nieh, Jenn–Yeu, et al., *Hot Plate Welding of Polypropylene. Part I: Crystallization Kinetics*, "Polymer Engineering and Science," Jul. 1998, vol. 38, No. 7, pp.–1121–1132.

Nieh, Jenn–Yeu, et al., *Hot Plate Welding of Polypropylene. Part II: Process Simulation*, "Polymer Engineering and Science," Jul. 1998, vol. 38, No. 7, pp. 1133–1141.

* cited by examiner

FIG._1A
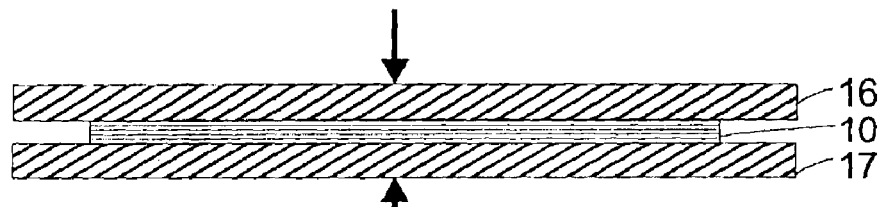
FIG._1B
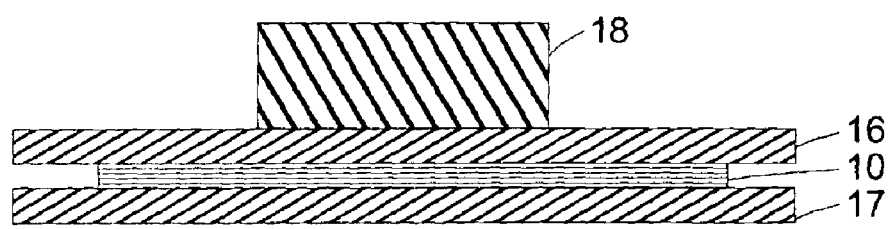
FIG._1C

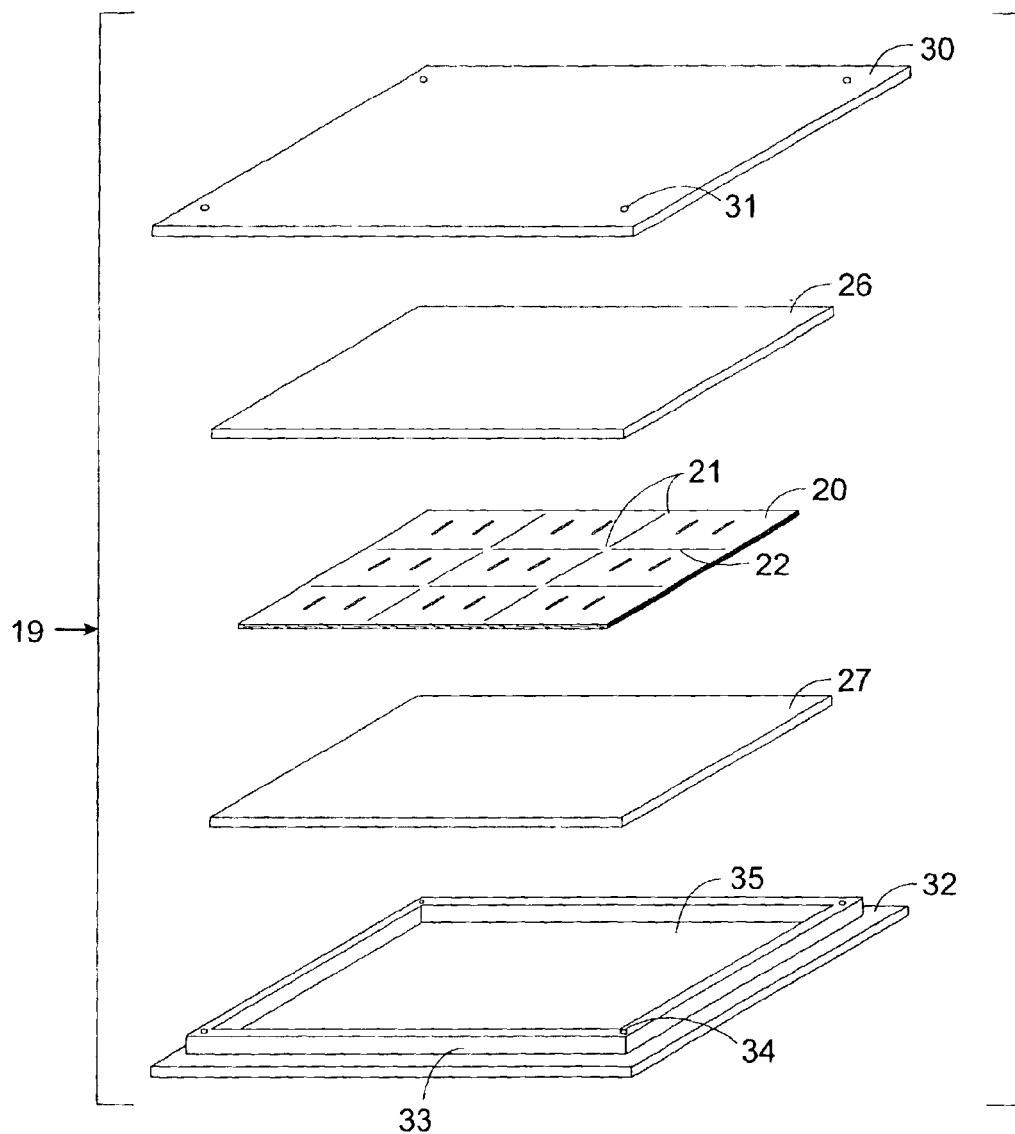
FIG._2A

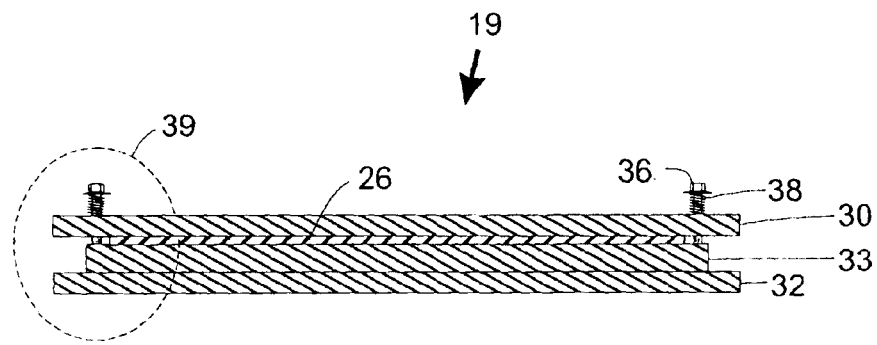
FIG._2B
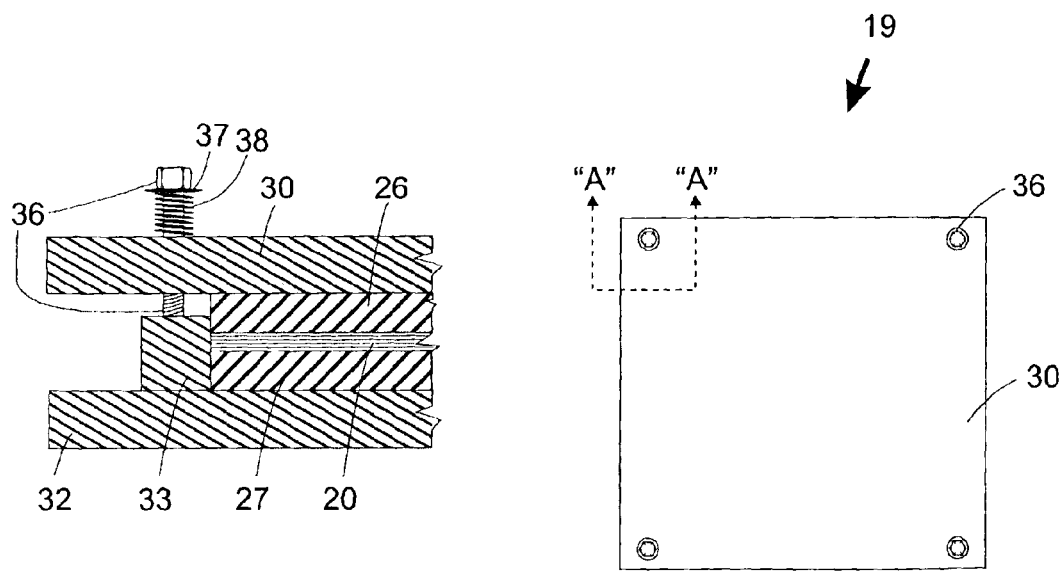
FIG._2C  FIG._2D

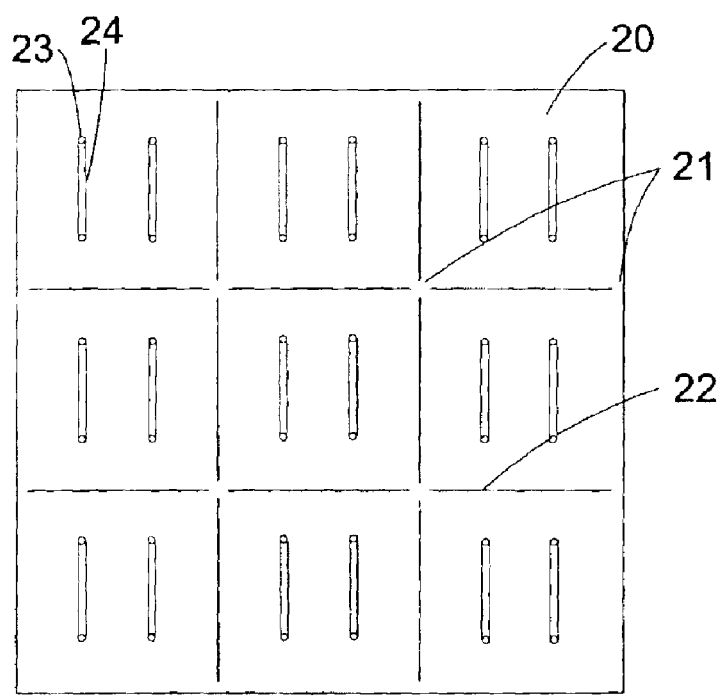
FIG._2E

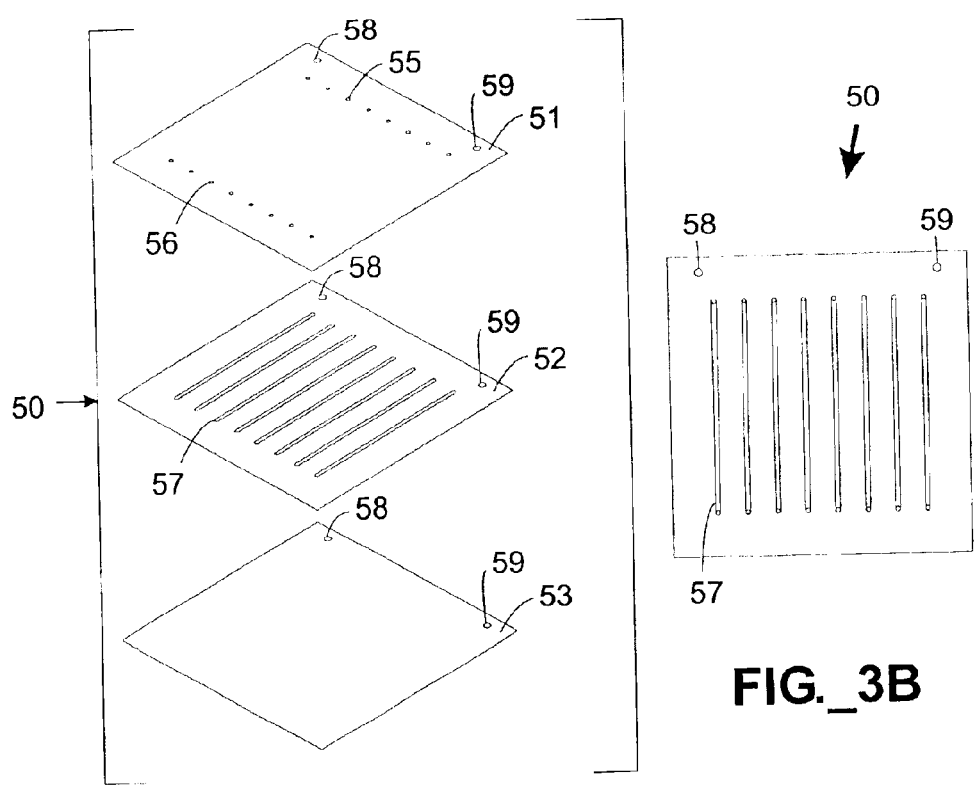
FIG._3A
FIG._3B

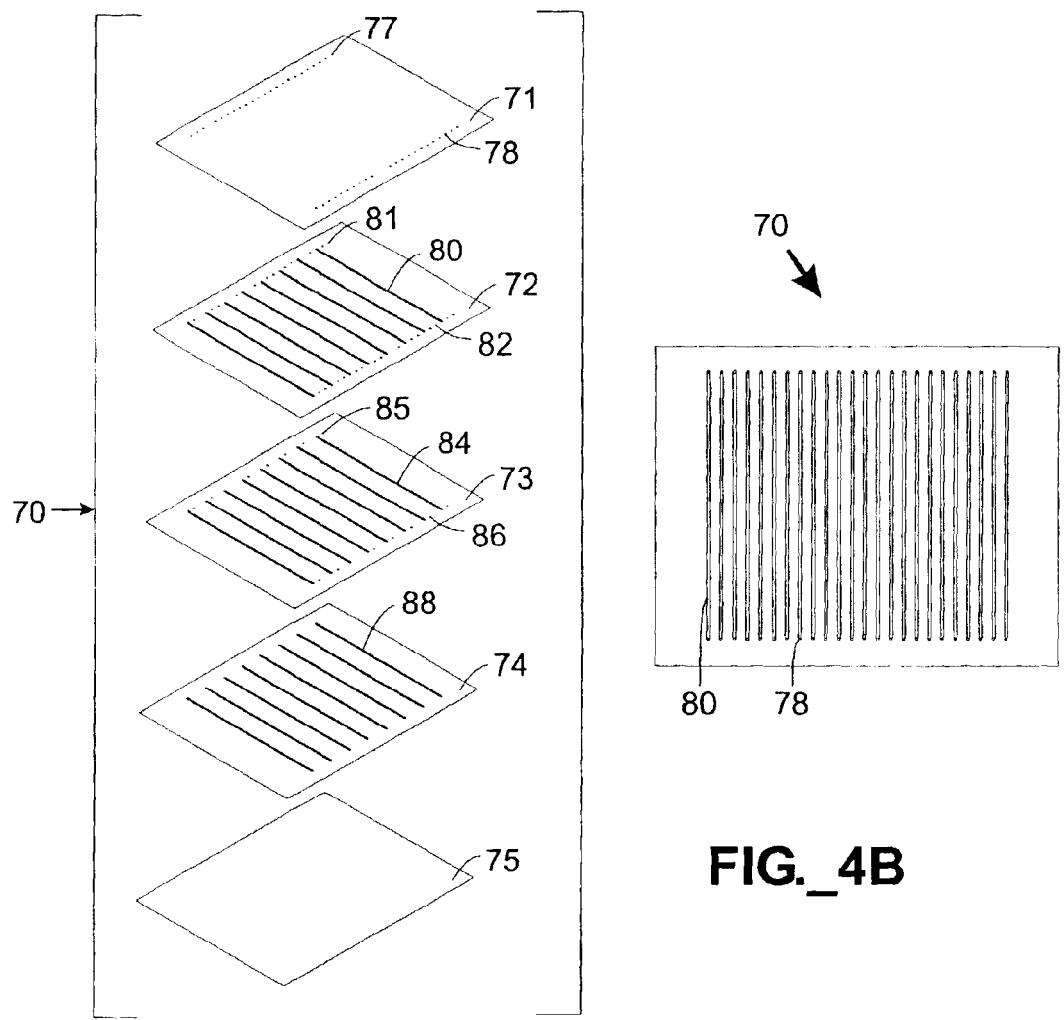
FIG._4A
FIG._4B

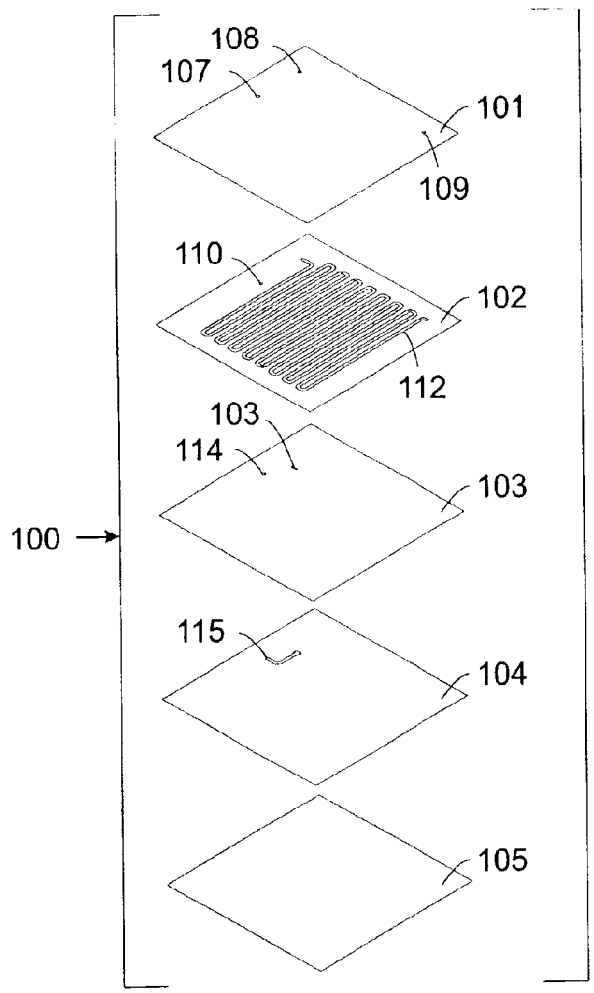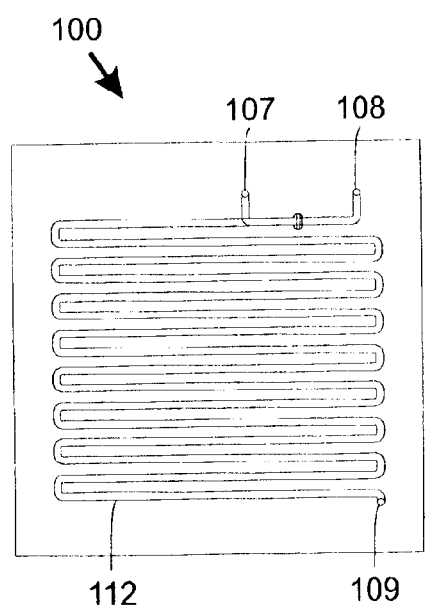
FIG._5A
FIG._5B

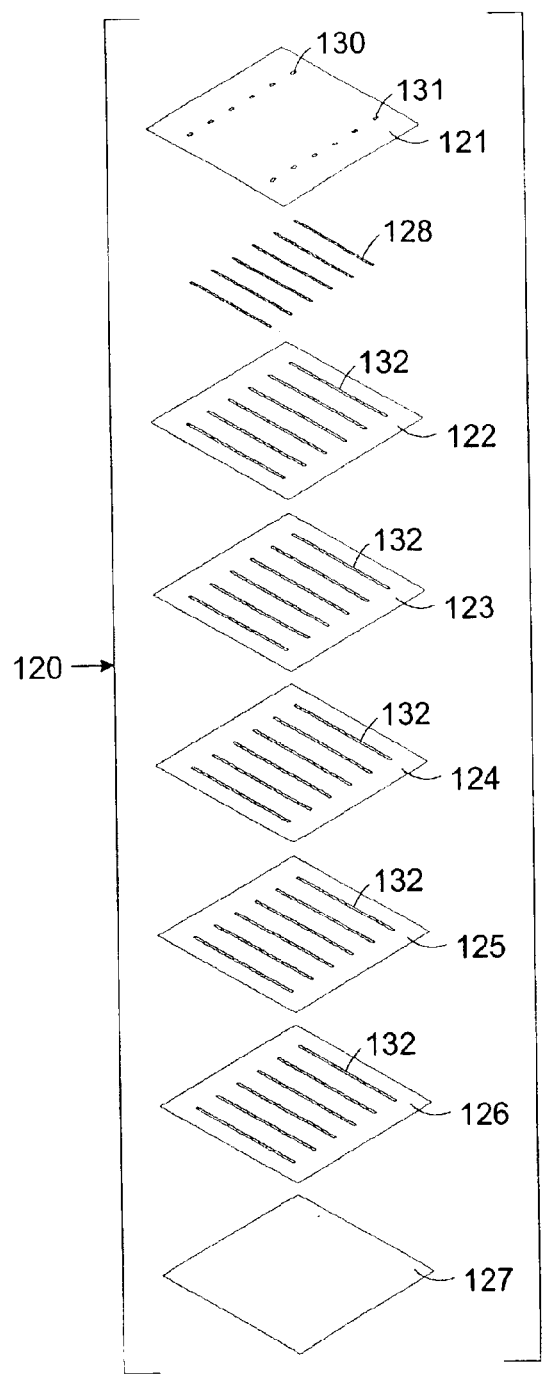
FIG._6A
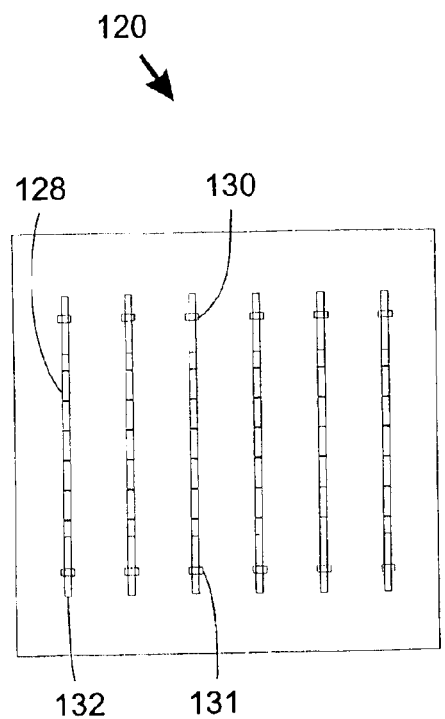
FIG._6B

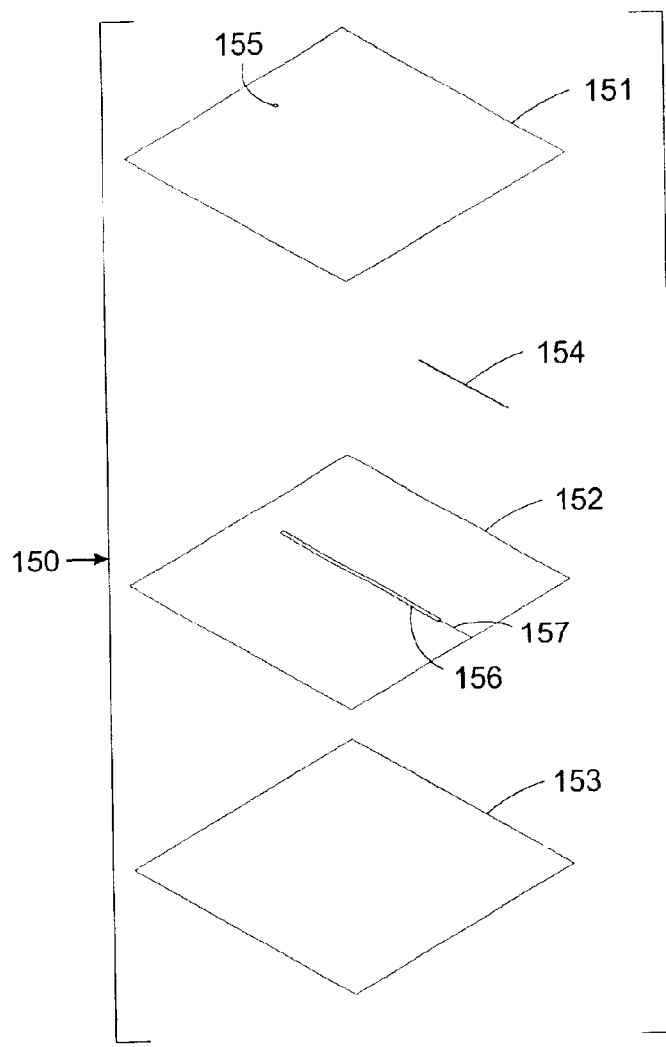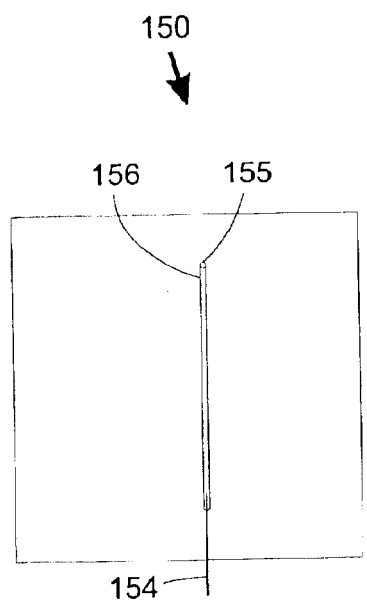
FIG._7A
FIG._7B

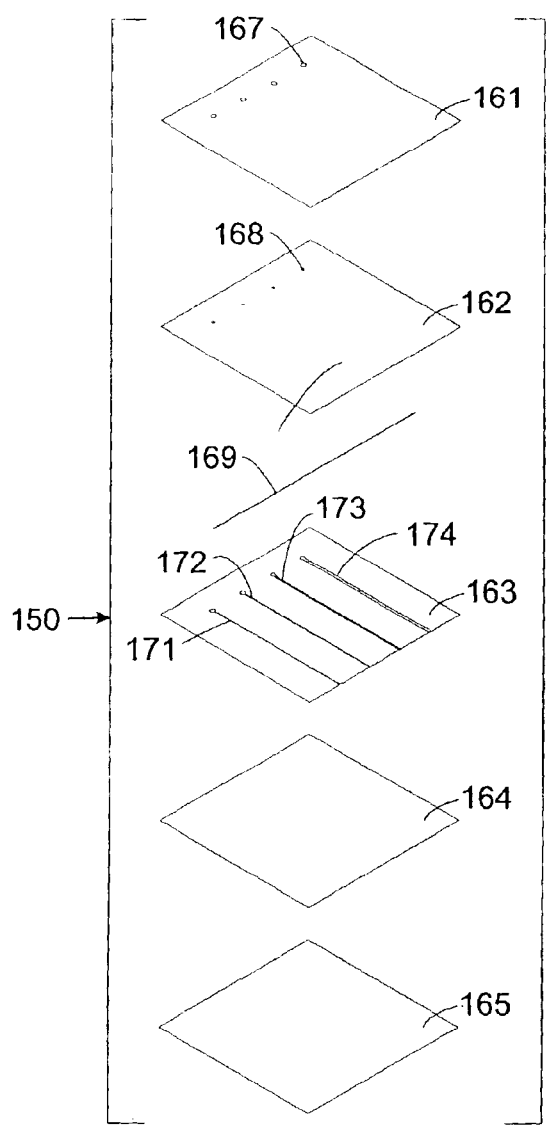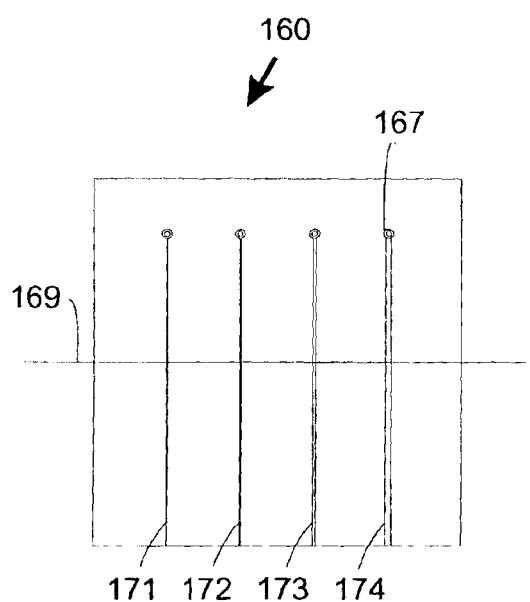
FIG._8A
FIG._8B

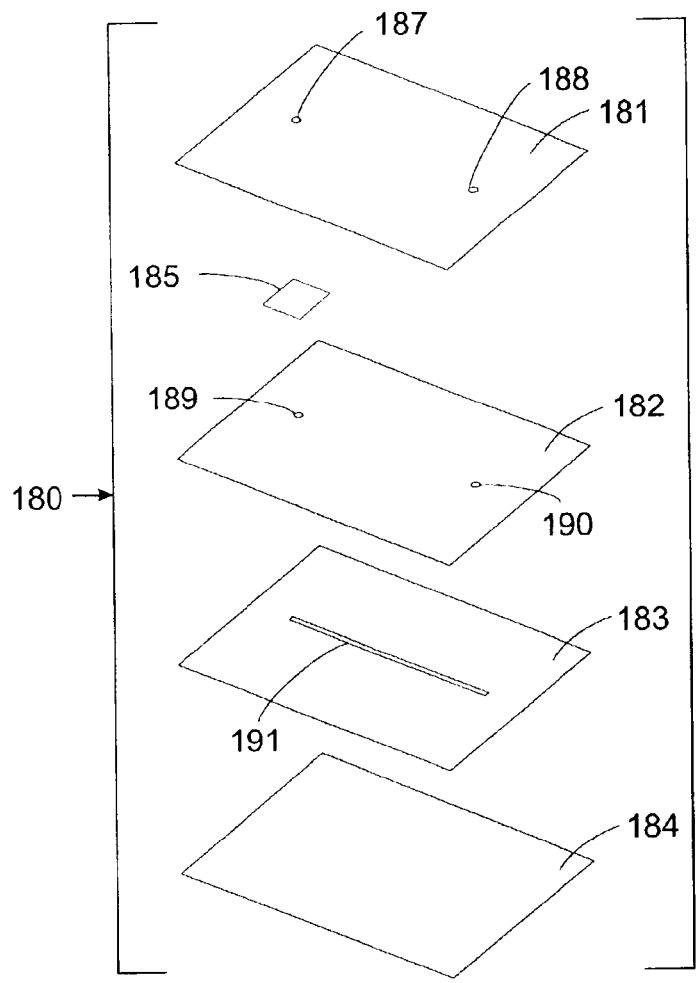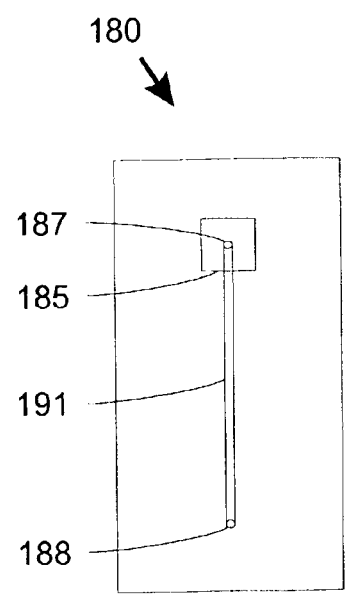
FIG._9A
FIG._9B

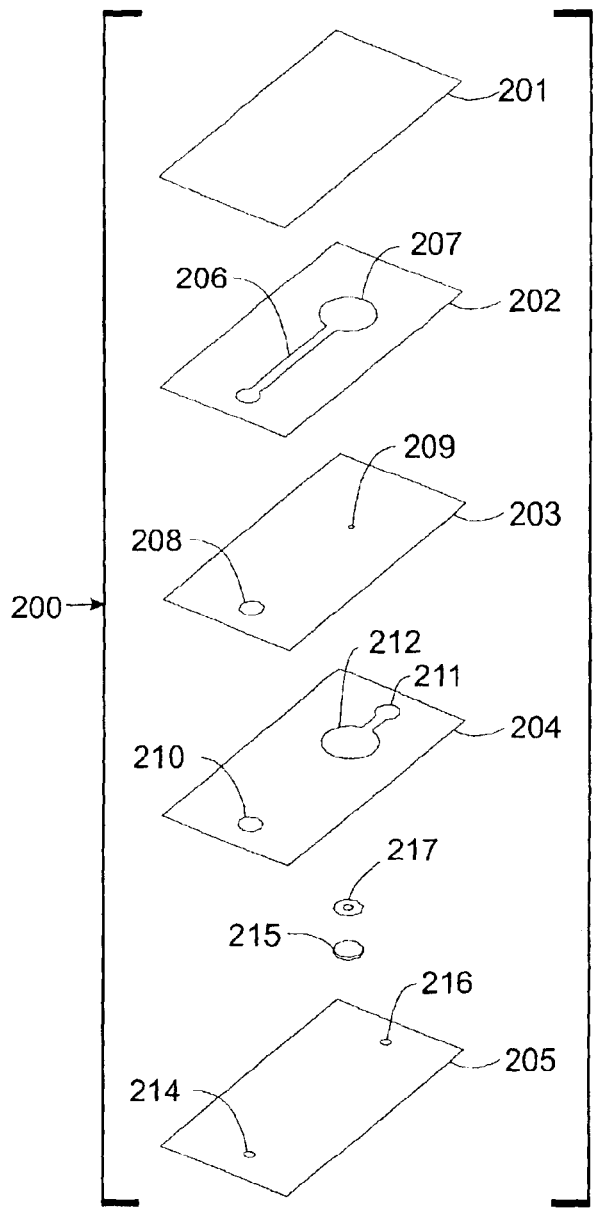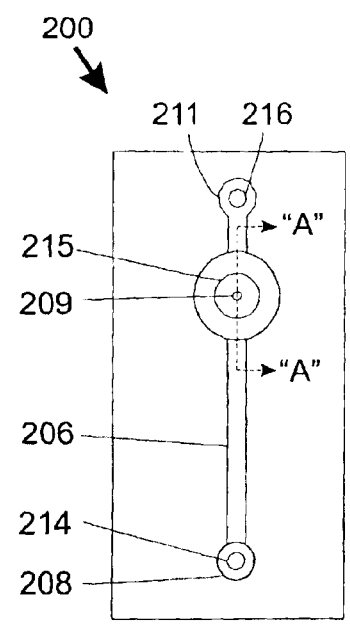
FIG._10A
FIG._10B

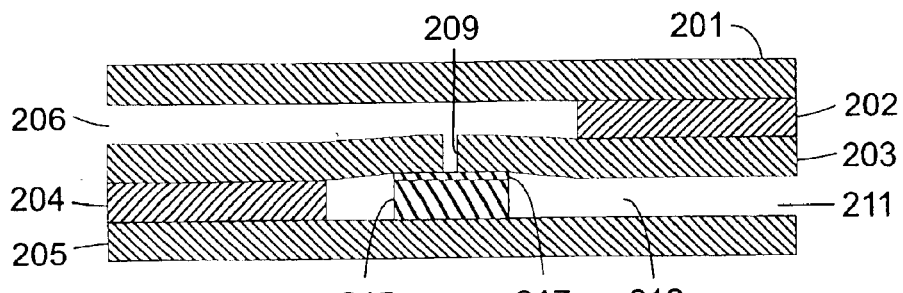
FIG._10C
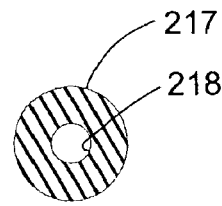
FIG._10D
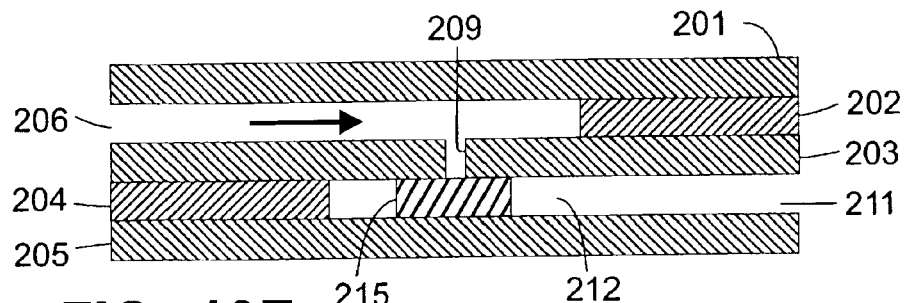
FIG._10E
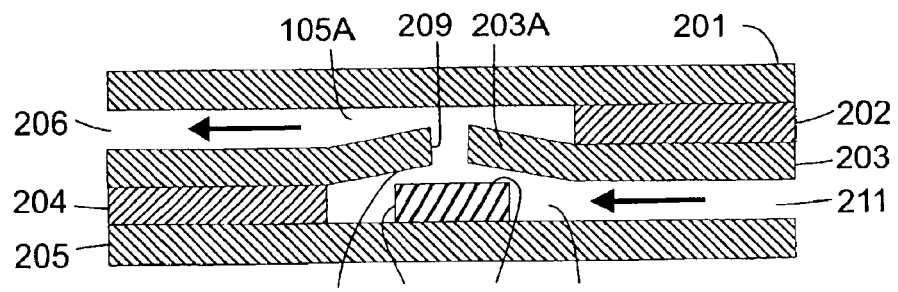
FIG._10F

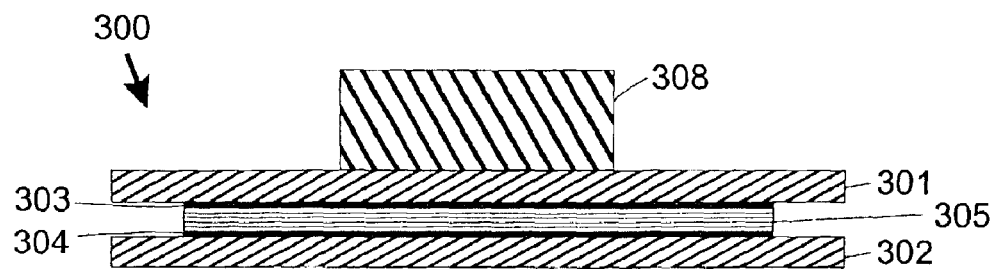
FIG._11
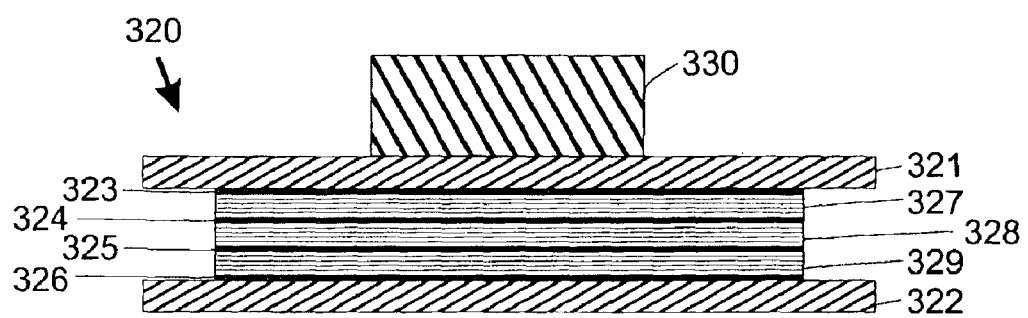
FIG._12

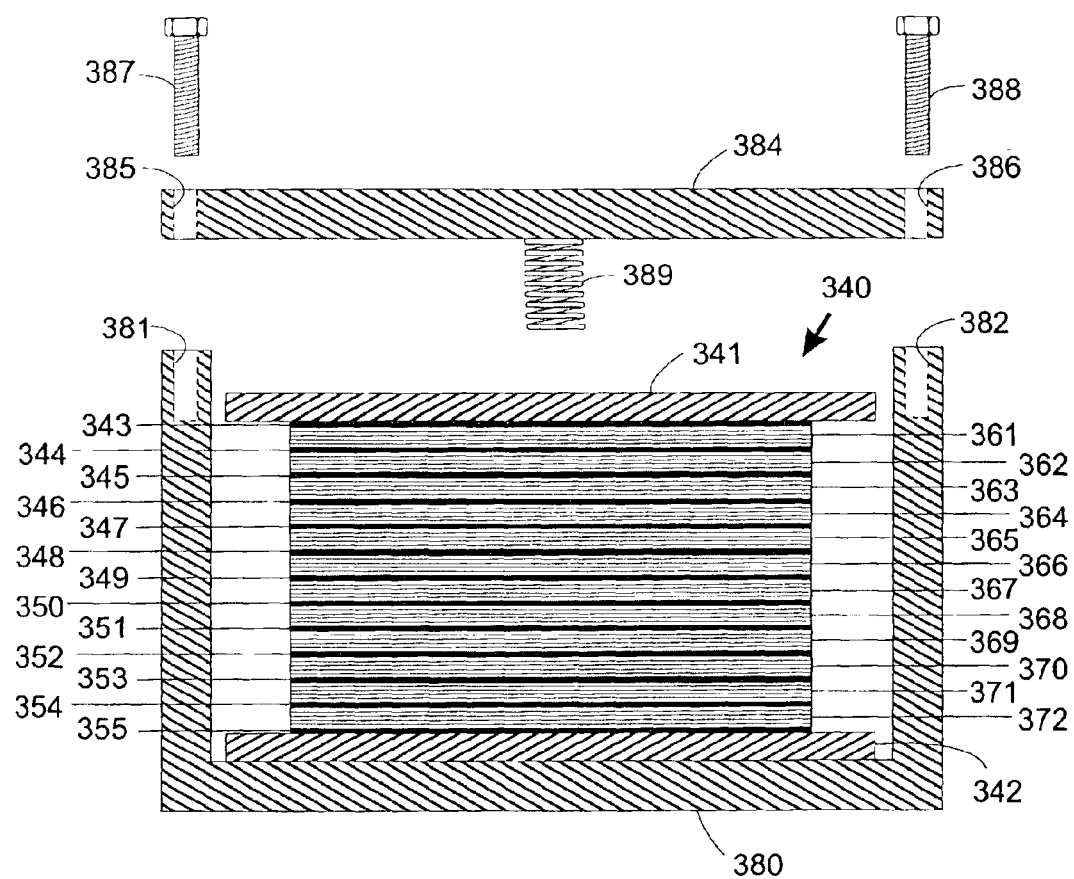
FIG._13

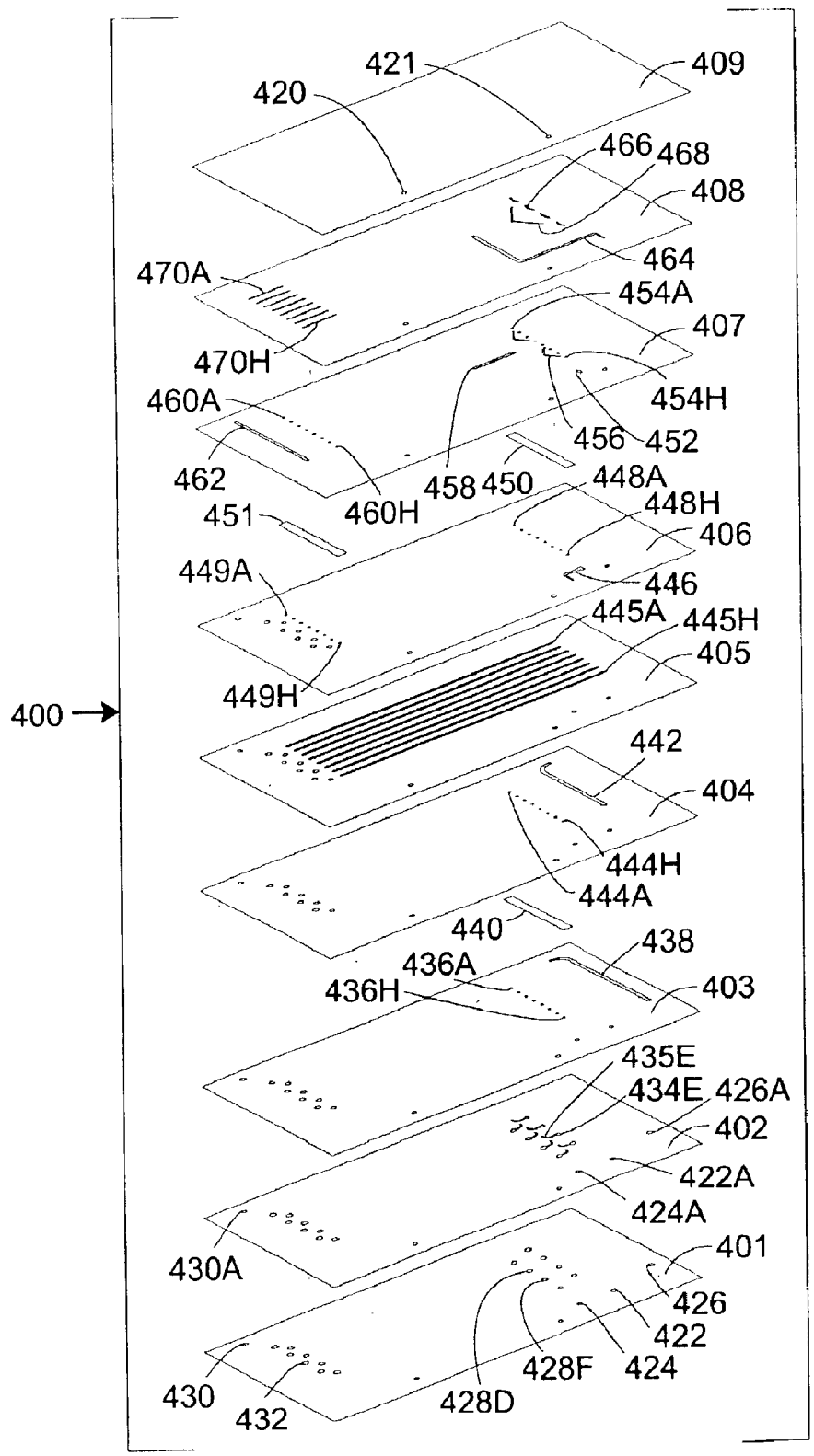
FIG._14A

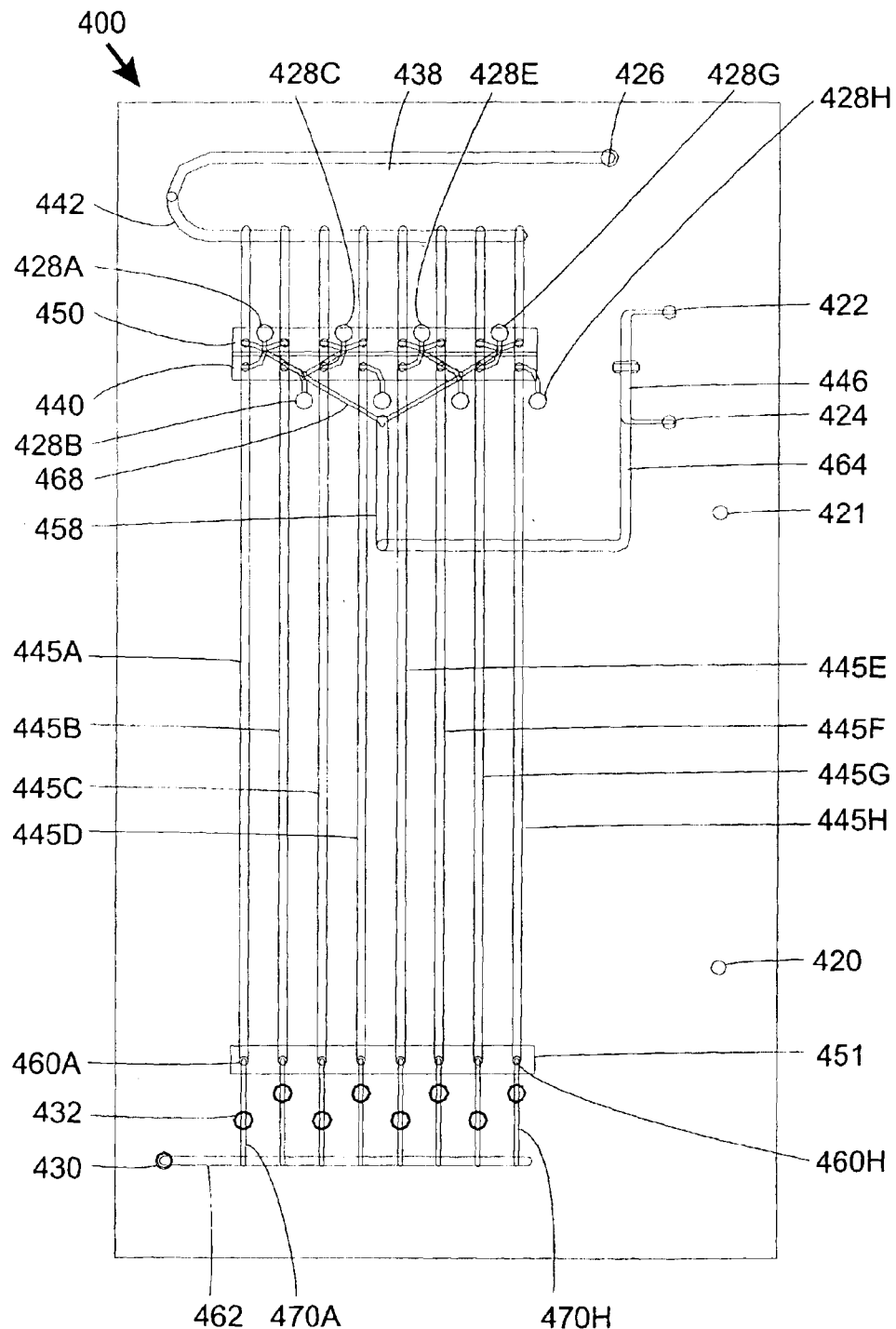
FIG._14B

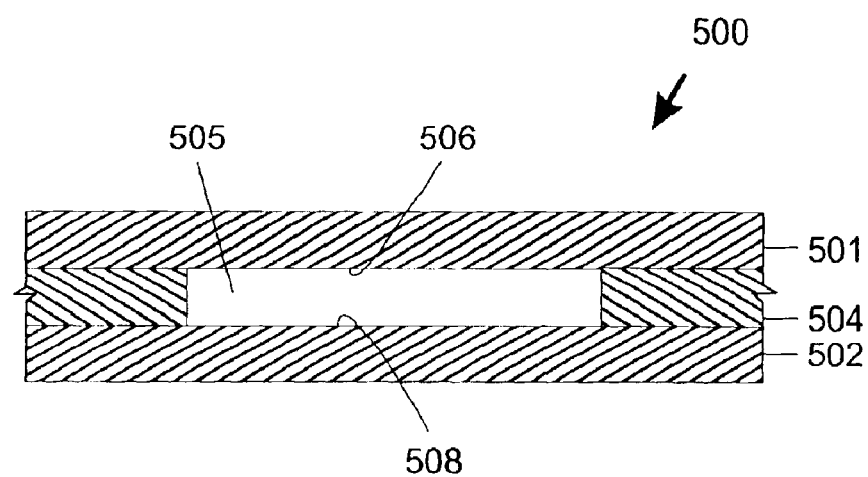
FIG._15

ADHESIVELESS MICROFLUIDIC DEVICE FABRICATION

STATEMENT OF RELATED APPLICATION(S)

This application claims priority to two commonly assigned U.S. Provisional Patent Applications, Ser. No. 60/338,286, filed Dec. 6, 2001 and Ser. No. 60/393,953, filed Jul. 2, 2002.

FIELD OF THE INVENTION

The present invention relates to the manufacture of microfluidic structures, i.e., structures for handling microscopic volumes of fluid.

BACKGROUND OF THE INVENTION

There has been a growing interest in the application of microfluidic systems to a variety of technical areas. For example, use of microfluidic systems for the acquisition of chemical and biological information presents certain advantages. In particular, when conducted in microfluidic volumes, complicated biochemical reactions and processes may be carried out using very small volumes of fluid. In addition to minimizing sample volume, microfluidic systems improve the response time of reactions and reduce reagent consumption. Furthermore, when conducted in microfluidic volumes, a large number of complicated biochemical reactions and/or processes may be carried out in a small area, such as in a single integrated device. Examples of desirable applications for microfluidic technology include analytical chemistry; chemical and biological synthesis, DNA amplification; and screening of chemical and biological agents for activity, among others.

Of the several different methods that have been developed for producing microfluidic devices, many utilize adhesives in their fabrication. For example, traditional methods for constructing microfluidic devices borrowed techniques borrowed from the silicon fabrication industry. According to these techniques, microfluidic devices have been constructed in a planar fashion and covered with a glass or similar cover materials to enclose fluid channels. Representative devices are described, for example, in some early work by Manz, et al. (Trends in Anal. Chem. (1990) 10(5): 144–149; Advances in Chromatography (1993) 33: 1–66). In these publications, microfluidic devices are constructed by using photolithography to pattern channels on silicon or glass substrates and etching techniques to remove material from the substrate to form the channels. A cover plate is bonded, typically using adhesives or anodic bonding, to the top of such a device to enclose the channels and contain a fluid flow.

More recently-developed methods that allow microfluidic devices to be constructed from plastic, silicone or other polymeric materials typically still require bonding of a cover to enclose fluidic channels. Such methods include micromolding of plastics or silicone using silicon as the mold material (see, e.g., Duffy et al., Anal. Chem. (1998) 70: 4974–4984; McCormick et al., Anal. Chem. (1997) 69: 2626–2630); injection-molding; and micromolding using a LIGA technique (see, e.g., Schomburg et al., Journal of Micromechanical Microengineering (1994) 4: 186–191), as developed at the Karolsruhe Nuclear Research Center in Germany and commercialized by MicroParts (Dortmund, Germany). LIGA and hot-embossing techniques have also been demonstrated by Jenoptik (Jena, Germany). Imprinting methods in polymethylmethacrylate (PMMA) have also been described (see, e.g., Martynova et al., Anal. Chem. (1997) 69: 4783–4789). Although mechanical or other attachment means may be employed, adhesives are commonly used to join a cover to a channel-containing planar microfluidic device.

While microfluidic devices fabricated with adhesives may be suitable for certain applications, their extension in other applications would be problematic. For example, adhesives may be susceptible to undesirable interaction with certain chemical solvents, particularly organic solvents. Undesirable interaction between such solvents and adhesives may vary in scope from relatively benign chemical reaction to more serious dissolution or chemical breakdown, leading to observable effects ranging from skewed detection results to structural failure of devices. Aside from these chemical interaction effects, adhesives in microfluidic devices may also interfere with biological reactions, such as, for example, non-specific binding studies.

Another potential limitation of adhesives—particularly pressure-sensitive adhesives—in fluidic devices is that adhesives are characterized by limited bond strength, which in turn limits the range of fluid pressures with which such devices may be operated. Typical pressure-sensitive adhesives are unsuitable for use in fluidic devices intended to handle pressures greater than approximately 100 psi (689.5 kPa). In applications such as liquid chromatography, it would be desirable to pack fluidic devices with stationary phase materials (e.g., using a slurry containing fine particles) at pressures greater of 500 psi (3450 kPa) (and preferably even higher pressures), and to operate such devices at pressures much greater than 100 psi (689.5 kPa).

Although methods have been developed for fabricating microfluidic devices in selected materials without using adhesives, such methods are not without other drawbacks. For example, multiple issued patents disclose the use of tin-enhanced polyimide materials to fabricate microfluidic structures. One such patent is U.S. Pat. No. 5,932,799, issued to Moles ("the Moles reference"). There, multi-layer microfluidic analyzer modules are fabricated without adhesives by directly bonding polyimide material layers enhanced with tin in a concentration between 400–10,000 ppm. Channels are formed in the surfaces of one or more layers by micromachining techniques such as photolithographic patterning followed by etching. Such layers are then physically compressed at a pressure between 24–690 bar (348–10,000 psi), preferably under vacuum at a sub-atmospheric internal pressure, and heated to a temperature between 350–455° C. for a period of about 5 minutes to 3 hours. The resulting structure of tin-containing polyimide material defines internal microfluidic channels along the interface between layers, and may be used to aid in detecting the presence of analytes.

Another reference describing adhesiveless microfluidic laminate structures fabricated from tin-enhanced (400 to 10,000 ppm) polyimide layers is U.S. Pat. No. 6,156,438, issued to Gumm, et al. ("the Gumm reference"). Mirror-imaged designs are formed on opposing inner facing surfaces of two tin-containing polyimide films using conventional micromachining techniques (e.g., chemical or laser etching). When two inner imaged films are subsequently superimposed in mirror relationship, channels and other structures for containing fluid flows may be formed along the interfaces between layers. The tin-containing polyimide layers may be attached by heat-pressure bonding (lamination) carried out at a temperature between 418–441° C. and a pressure between 250–450 psi for a period between 5 and 15 minutes.

Both the Moles and Gumm references require the addition of metallic (i.e., tin) ions to polyimide layers in order to achieve satisfactory bonding. The presence of metal ions limits the utility of such devices in several applications. In one desirable microfluidic application, chromatography, the presence of metal ions would be detrimental for several reasons. For example, metal ions can contaminate stationary phase material, thus rendering the stationary phase material incapable of performing its intended separation of a sample. Additionally, many mobile phase solvents will cause leaching of metal ions into the mobile phase, thus causing detection problems such as extraneous peaks and/or signal drift.

The presence of metal ions can also problematic in other microfluidic applications involving biological moieties. Specifically, metal ions are known to interact with biological materials such as enzymes, proteins, and cells. In microfluidic devices fabricated with metal ions, it may be difficult to execute controlled experiments using biological materials.

Moreover, the Moles and Gumm references are limited to the use of polyimides, which may have limited applicability in certain microfluidic applications. From a material compatibility perspective, polyimides are susceptible to hydrolysis when subjected to alkaline solvents, thus precluding their reliable use in applications such as chemical synthesis. Optical properties present another drawback in using polyimides. Because polyimides are generally opaque to many useful light spectra, they are ill-suited for use with many proven detection technologies that are commonly used in analytical chemistry. Further, an impaired ability to see into microfluidic devices also inhibits experimental use and quality control verification. Finally, both the Moles and Gumm references disclose the fabrication of channels using time-consuming surface micromachining techniques such as photolithography coupled with etching techniques, which requires high setup costs.

Adhesiveless bonding of polymer layers is generally well-known and widely used for applications outside the regime of microfluidic device fabrication. For example, a textbook describing polymer bonding is "Joining of Plastics: Handbook for Designers and Engineers" by Jordan Rotheiser, Hanser Gardner Publications, Inc., Cincinnati, Ohio (1999). Typically, if a structure having more than two layers is desired, such a structure is fabricated one interface at a time. In other words, most conventional multi-layer polymer structures are fabricated sequentially, such as by first joining two thin polymer films to yield a thick film, then joining another thin film to the thick film to yield a thicker film, and so on. Conventional methods include hot plate welding and hot gas welding (wherein which the surface(s) of one or both layers to be joined are melted and then contacted or pressed together) and hot roll lamination involving one or more heated rollers. Conventional applications for laminated polymer layers do not require precise inter-layer alignment—but even if such alignment were required, sequential joining methods would be limiting in this context because each joining step inherently causes significant dimensional distortion (e.g. thinning, shrinkage in one direction, and/or elongation in another direction), and the combined effect of several distortions would render precise alignment practically impossible.

Moreover, in typical applications involving adhesiveless bonding of polymer layers, small internal features are not present, and the practitioner need not be concerned with maintaining the integrity of such features. As a result, in most applications involving adhesiveless polymer layer bonding, the polymer interfaces are melted to a degree that there is significant material flow at the interface to achieve maximum bond strength. Thus, if precise features were provided in the layers prior to bonding, such features would be unlikely to survive conventional bonding processes.

In light of the foregoing, it would be desirable to be able to fabricate adhesiveless and substantially metal-free microfluidic structures having high bond strength (so as to permit leak-free fluidic operation at high pressures), yet being free of collapsed regions (that would lead to unpredictable fluid flow within the microstructures). It would be desirable if such structures could be fabricated from a range of different materials, including substantially colorless materials to provide compatibility with established optical detection techniques and quality control methods. It would also be desirable if such structures could be fabricated with minimal dimensional distortion of internal and external features. It would be further desirable if such structures could be prototyped and fabricated quickly at a low cost.

SUMMARY OF THE INVENTION

In a first separate aspect of the invention, a method for fabricating a microfluidic device several method steps. A first method step includes providing a first and a second substantially flat platen. A second method step includes providing multiple substantially planar, substantially metal-free, adhesiveless polymer device layers, the device layers including a first cover layer, second cover layer, and at least one stencil layer defining a microfluidic channel penetrating through the entire thickness of the stencil layer. Each stencil layer is disposed between other device layers such that the channel is bounded laterally by a stencil layer, and bounded from above and below by surrounding device layers to define an upper channel surface and a lower channel surface. A third method step includes stacking the device layers between the first platen and the second platen. A fourth method step includes controllably heating the stacked device layers according to a heating profile adapted to form a substantially sealed adhesiveless microfluidic device wherein each upper channel surface remains distinct from its corresponding lower channel surface. The resulting microfluidic device has high inter-layer bond strength while preserving the integrity of the channel(s) defined in the stencil layer(s). Additional steps may be employed to enhance the fabrication method.

In another separate aspect of the invention, a method for fabricating a plurality of microfluidic devices simultaneously includes several method steps. A first method step includes providing a first and a second substantially flat, thermally insulating platen. A second method step includes providing multiple thin thermally conducting layers. A third method step includes providing multiple groups of substantially planar, substantially metal-free, adhesiveless polymer device layers, each group including at least one stencil layer defining a microfluidic channel penetrating through the entire thickness of the stencil layer. Each stencil layer is disposed between other device layers within the same group such that the channel is bounded laterally by a stencil layer, and bounded from above and below by surrounding device layers to define an upper channel surface and a lower channel surface. A fourth method step includes stacking the multiple groups of device layers, the thermally conducting layers, and the platens, with the first platen and the second platen on the outside, and with each group of polymer layers disposed between two thermally conducting layers of the plurality of thermally conducting layers. A fifth method step includes controllably heating the groups of device layers according to a heating profile adapted to bond each group of device layers into a substantially sealed microfluidic device wherein the upper channel surface remains distinct from the lower channel surface. Each resulting microfluidic device has high inter-layer bond strength while preserving the integrity of the channel(s) defined in the stencil layer(s). Additional steps may be employed to enhance the fabrication method.

In another separate aspect of the invention, an adhesiveless microfluidic device is fabricated with multiple substantially planar, substantially metal-free, adhesiveless polymer device layers including a first and a second cover layer and at least one stencil layer disposed between the cover layers. The stencil(s) defines at least one microfluidic channel through the entire thickness of the stencil, such that each channel is bounded laterally by a stencil layer and bounded from above and below by additional device layers to form an upper channel surface and a lower channel surface. The device layers are interpenetrably bound together to form a substantially sealed adhesiveless microstructure with the upper surface remaining distinct from the lower surface. The resulting microfluidic device has high inter-layer bond strength while preserving the integrity of the channel(s) defined in the stencil layer(s). In further embodiments, additional materials may be optionally included. For example, functional items such as porous membranes, electrical conductors, electrospray needles, capillary tubes, and sensors may be disposed at least partially within a microstructure. Further, inert or degradable materials may be optionally provided between device layers in certain regions to prevent permanent bonding between device layers along such regions.

In another separate aspect of the invention, any of the foregoing aspects may be combined for additional advantage.

These and other aspects and advantages of the present invention will become apparent upon reviewing the detailed description, drawings, and appended claims.

BRIEF DESCRIPTION OF THE DRAWINGS

FIG. 1A is a side view of multiple adhesiveless device layers sandwiched between platens, the device layers including at least one stencil layer defining a microfluidic channel. FIG. 1B illustrates the same view as FIG. 1A, but further includes arrows indicating the application of a compressive force to the platens and device layers. FIG. 1C illustrates the same view as FIG. 1A, but further includes a weight for applying a compressive force to the platens and device layers.

FIG. 2A is an exploded perspective view of several components of a compressive jig assembly for applying a compressive force to device layers to form an array of nine interconnected microfluidic devices disposed between platens. FIG. 2B is a side view of the assembled compressive jig assembly of FIG. 2A, showing the addition of compression springs affixed with threaded bolts. FIG. 2C is an expanded side sectional view of the circled portion 39 of FIG. 2B along section lines "A—A" provided in FIG. 2D. FIG. 2D is a top view of the assembled compressive jig assembly of FIG. 2B. FIG. 2E is a top view of the array of nine interconnected adhesiveless microfluidic devices illustrated in FIG. 2A, the array having scored regions between individual devices.

FIG. 3A is an exploded perspective view of a three-layer adhesiveless microfluidic device defining multiple channels in a central stencil layer. FIG. 3B is a top view of the assembled device of FIG. 3A.

FIG. 4A is an exploded perspective view of a five-layer adhesiveless microfluidic device defining 24 channels in three stencil layers. FIG. 4B is a top view of the assembled device of FIG. 4A.

FIG. 5A is an exploded perspective view of a five-layer adhesiveless microfluidic mixing reactor device including multiple stencil layers. FIG. 5B is a top view of the assembled device of FIG. 5A.

FIG. 6A is an exploded perspective view of a seven-layer adhesiveless microfluidic device having six embedded capillary tubes. FIG. 6B is a top view of the assembled device of FIG. 6A.

FIG. 7A is an exploded perspective view of a three-layer adhesiveless microfluidic device having an embedded electrospray needle. FIG. 7B is a top view of the assembled device of FIG. 7A.

FIG. 8A is an exploded perspective view of a five-layer adhesiveless microfluidic device having an embedded wire in electrical contact with each of five channels defined in a central stencil layer. FIG. 8B is a top view of the assembled device of FIG. 8A.

FIG. 9A is an exploded perspective view of a four-layer adhesiveless microfluidic device having an encapsulated porous membrane and a single channel-defining stencil layer. FIG. 9B is a top view of the assembled device of FIG. 9A.

FIG. 10A is an exploded perspective view of a five-layer microfluidic uni-directional valve device, the layers of the device bonded together with an adhesiveless bonding method. FIG. 10B is a top view of the assembled device of FIG. 10A. FIG. 10C is a cross-sectional view of a portion of the device of FIGS. 10A–10B taken along section lines "A—A", showing the inclusion of a degradable material in the device. FIG. 10D is a top view of the degradable material of FIG. 10C. FIGS. 10E–10F provide the same views as FIG. 10C, but illustrate the device in different states of operate following degradation and removal of the degradable material.

FIG. 11 is a side view of a single group of multiple adhesiveless polymer device layers disposed between thin thermally conducting layers and further between thermally insulating platens, the device layers including at least one stencil layer defining a microfluidic channel.

FIG. 12 is a side view of a multiple groups of adhesiveless polymer device layers disposed between thin thermally conducting layers and further between thermally insulating platens, each group of device layers including at least one stencil layer defining a microfluidic channel.

FIG. 13 is an exploded side cross-sectional view of an enclosed apparatus useful to bond multiple stacks of adhesiveless polymer layers into multiple substantially sealed microfluidic devices.

FIG. 14A is an exploded perspective view of an adhesiveless nine-layer microfluidic separation device having multiple stencil layers defining eight separation columns and related fluidic channel networks, the device further including three porous membranes. FIG. 14B is a top view of the device of FIG. 14A.

FIG. 15 is a cross-sectional view of at least a portion of a stencil based adhesiveless microfluidic device illustrating a microfluidic channel.

DETAILED DESCRIPTION OF PREFERRED EMBODIMENTS OF THE INVENTION

Definitions

Figure 16:
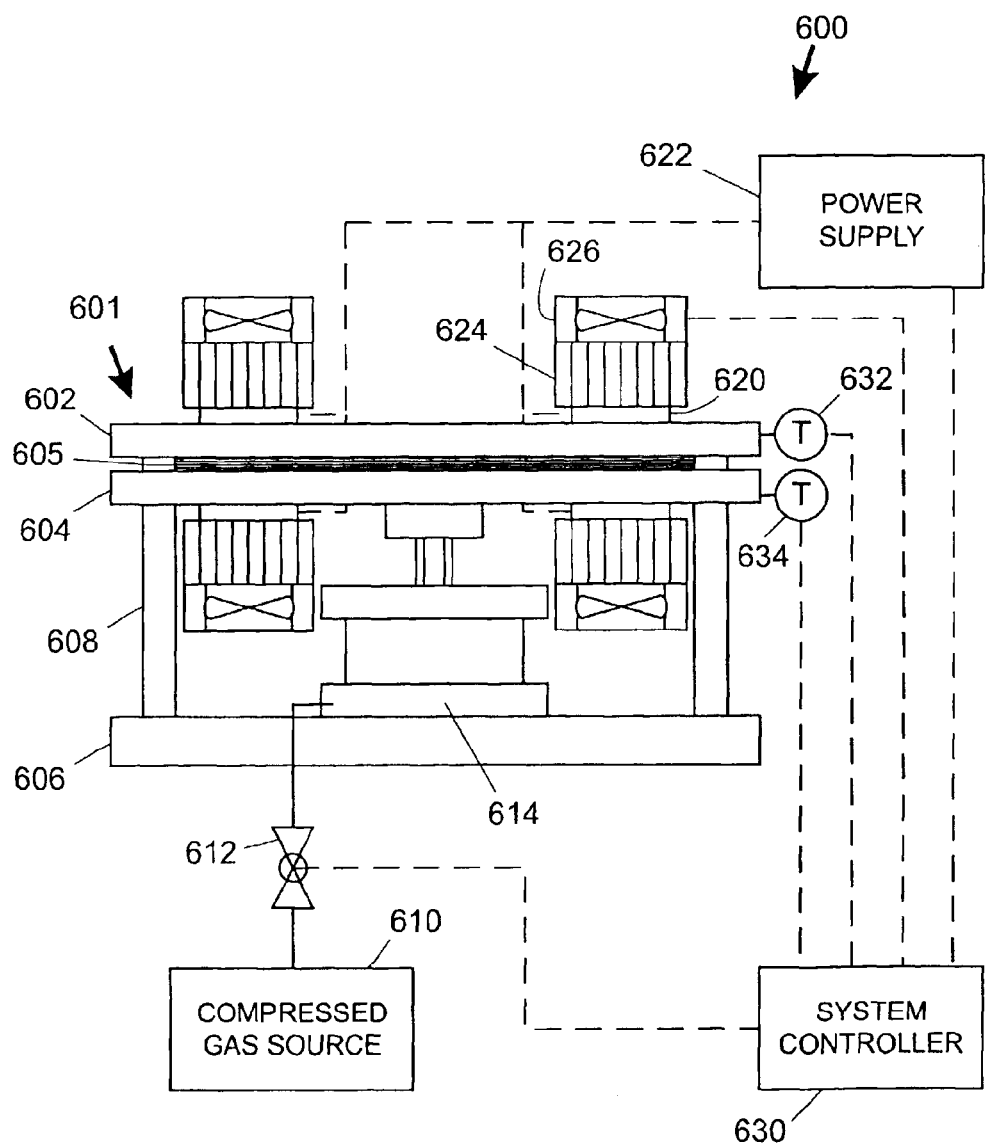
FIG. 16 is a schematic of a heated platen system permitting controlled heating and cooling of, as well the controlled application of pressure, to adhesiveless device layers, the system suitable for performing methods described herein.

The term "adhesiveless" as used herein refers to the state of lacking any substance adapted to stick, bond, or otherwise adhere one surface to another. Notably, in certain embodiments wherein degradable adhesives are used to prevent permanent bonding between device layers and the degradable adhesive is subsequently removed, the term "adhesiveless" is intended to apply to the resulting device following removal of substantially all of the degradable adhesive.

The term "channel" as used herein is to be interpreted in a broad sense. Thus, it is not intended to be restricted to elongated configurations where the transverse or longitudinal dimension greatly exceeds the diameter or cross-sectional dimension. Rather, the term is meant to include cavities, tunnels, or chambers of any desired shape or configuration through which fluids be directed. A channel may be substantially filled with a packing material or may contain one or more functional structures such as valves or equivalent components.

The term "degradable material" as used herein refers to a material that may be degraded without destroying or otherwise impairing the use of a surrounding microstructure. Various processes may be used to accomplish such degradation, including, for example, chemical dissolution.

As used herein, the terms "differential scanning calorimetry melting point" and "DSC melting point" for a particular polymer are used interchangeably and refer to the temperature corresponding to the minimum heat flux in the solid/liquid phase change portion of the thermogram (heat flux versus temperature) of the polymer.

The term "interpenetrably bound" as used herein refers to the condition of two adjacent polymer surfaces being bound along a substantially indistinct interface resulting from diffusion of polymer chains from each surface into the other.

The term "microfluidic" as used herein is to be understood to refer to structures or devices through which one or more fluid(s) are capable of being passed or directed, wherein one or more of the dimensions of any fluidic passage defined therein is less than about 500 microns.

The term "stencil" as used herein refers to a material layer or sheet that is preferably substantially planar, through which one or more variously shaped and oriented portions has been cut or otherwise removed through the entire thickness of the layer, and that permits substantial fluid movement within the layer (e.g., in the form of channels or chambers, as opposed to simple through-holes for transmitting fluid through one layer to another layer). The outlines of the cut or otherwise removed portions form the lateral boundaries of microstructures that are formed when a stencil is sandwiched between substrates and/or other stencils.

The term "substantially metal-free" as used herein means substantially free of metals, metal ions, and organometallic compounds.

The term "substantially sealed" as used herein refers to the condition of having a sufficiently low unintended leakage rate and/or leakage volume under given flow, fluid identity, or pressure conditions. Types of unintended leakage include leakage or pooling that accumulates in unintended regions between device layers and leakage to an environment outside a microfluidic device. A substantially sealed microstructure is contemplated to have one or more fluidic ports or apertures to provide desirable fluidic inlet or outlet utility.

The terms "thermal conductor" or "thermally conducting" as used herein refers generally to metals, silicon, and other materials having similarly high thermal conductivities. For example, approximate thermal conductivity values [W/cm-K] for selected thermal conductors follow: copper: 3.937; aluminum: 2.165; silicon: 1.457; platinum: 0.734; low carbon steel: 0.669; stainless (321) steel: 0.146.

The terms "thermal insulator" or "thermally insulating" as used herein refers to generally to glasses, polymers, and other materials having similarly low thermal conductivities. For example, approximate thermal conductivity values [W/cm-K] for selected thermal insulators follow: glass: 0.008; FR-4 or G-10 PC board material: 0.003; poly (ethylene terephthalate): 0.002; polytetrafluoroethylene: 0.002.

The term "thermal mass" as used herein refers to the ability of an object to absorb thermal energy. Thermal mass may be quantified as the product of an object's mass and its heat capacity (the amount of heat transferred to raise unit mass of a material one degree in temperature). Since for most engineering purposes heat capacities may be assumed to be numerically equal to specific heats, specific heat (the ratio of the amount of heat transferred to raise unit mass of a material 1 degree to that required to raise unit mass of water 1 degree as some specified temperature) may be substituted for heat capacity in the product described above.

The term "thin" as used herein and applied to a thermally conducting layer is used in a relative sense, as compared to a thermally insulating platen used in conjunction with the thermally conducting layer to facilitate bonding of an adhesiveless polymeric microfluidic device. The term "thin" refers to the relative thermal mass of a thermally conducting layer compared to a thermally insulating platen; specifically, to be deemed "thin," a thermally conducting layer should preferably have a thermal mass of less than about one-half of the thermal mass of an associated thermally insulating platen; more preferably the thermally conducting layer should have a thermal mass of less than about one-tenth of the thermal mass of an associated thermally insulating platen; and even more preferably the thermally conducting layer should have a thermal mass of less than about one-fiftieth of the thermal mass of an associated thermally insulating platen.

Microfluidic Device Fabrication Generally

In especially preferred embodiments, microfluidic devices according to the present invention are constructed using stencil layers or sheets to define channels and/or chambers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut patterns through a material layer. While laser cutting may be used to yield precisely-dimensioned microstructures, the use of a laser to cut a stencil layer inherently removes some material. Further examples of methods that may be employed to form stencil layers include conventional stamping or die-cutting technologies. Any of the above-mentioned methods for cutting through a stencil layer or sheet permits robust devices to be fabricated quickly and inexpensively compared to conventional surface micromachining or material deposition techniques used by others to produce fluidic microstructures.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. Preferred layer thicknesses are less than or equal to about 10 mils (250 microns). When assembled in a microfluidic device, the top and bottom surfaces of stencil layers are intended to mate with one or more adjacent stencil or substrate layers to form a substantially enclosed device, typically having one or more inlet ports and one or more outlet ports.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

Although less preferred, other conventional methods (e.g., micromachining, soft lithography, micromolding, etc.) may be used to define microfluidic channels in one or more layers of a microfluidic device prior to adhesiveless bonding according to methods disclosed herein.

Materials

Preferably, materials used in accordance with the present invention are adhesiveless and substantially metal-free, for the reasons discussed previously. Preferred materials for use in fabricating microfluidic devices according to the present invention include substantially colorless polymer layers to provide favorable optical properties. Because most substantially colorless polymers are transparent to useful light spectra, they are well-suited for use with a variety of different detection technologies that are commonly used in analytical chemistry. The ability to see into a microfluidic device further aids in device testing, optimization, and quality control verification.

Preferably, polymers used with the present invention are unoriented to minimize unpredictable shrinkage and distortion. In polymer film technology, unoriented films are typically fabricated by casting methods.

Further subclasses of preferred materials include alkene-based (i.e., vinyl-based) polymers, and more specifically polyolefins, including both halogenated and non-halogenated varieties. Most alkene-based polymers, particularly polyolefins, are desirable for their general resistance to chemical attack and compatibility with a variety of chemicals and biological moieties, coupled with favorable mechanical properties including relatively high tensile strength and relatively high thermal resistance. Particularly preferred polyolefins include polypropylenes (generally including both homopolymers and copolymers) and polyethylenes.

Less preferred materials include polyesters, polycarbonates, polyamides, and polyimides. As compared to polyolefins, these materials exhibit reduced bond strength, as a percentage of the (e.g., tensile) strength of the base material.

Complex Microfluidic Devices

Adhesiveless microfluidic devices according to both simple and highly complex designs may be fabricated according to methods described herein. For example, adhesiveless devices having progressively more complex designs are illustrated in FIGS. 3A–3B, 5A–5B, and 4A–4B.

One example of a highly complex, utilitarian adhesiveless microfluidic device is illustrated in FIGS. 14A–14B. There, a microfluidic separation device 400 includes eight separation channels 445A–445H and eight discrete sample inputs 428A–428H to permit eight different samples to be separated simultaneously using liquid chromatography. The device 400 is constructed with nine device layers 401–409, including multiple stencil layers 402–408. Each of the nine layers 401–409 defines two alignment holes 420, 421, which are used in conjunction with external pins (not shown) to aid in aligning the layers 401–409 during construction, and/or to aid in aligning the device 400 with an external interface (not shown) during a separation channel packing process. The first layer 401 defines several fluidic ports: two solvent inlet ports 422, 424 that may be used to admit different (mobile phase) solvents to the device 400; eight sample ports 428A–428H that permit sample to be introduced to eight separation channels 445A–445H or "columns" (each containing stationary phase material); a slurry inlet port 426 that is used during a column packing procedure to admit slurry to the device 400; and a fluidic port 430 that is used (1) during a slurry packing process to exhaust solvent (separated from slurry) from the device 400; and (2) during operation of the separation device 400 to exit mobile phase solvent and sample from the device 400 following separation. The first through sixth layers 401–406 each define eight optical detection windows 432. Defining these windows 432 through the first six layers 401–406 facilitates optical detection since it reduces the amount of material between an optical detector (not shown) such as a conventional UV-VIS spectrometer/detector, and the samples contained in channel segments 470A–470H downstream of the separation channels 445A–445H.

The second through seventh layers 402–407 each define solvent vias 422A to transport a first mobile phase solvent to a solvent channel 464 defined in the eighth layer 408, with further solvent vias 424A defined in the second through fifth layers 402–405 to transport a second mobile phase solvent to a second solvent channel 446 defined in the sixth layer 406. Further vias 430A are defined in the second through sixth layers 402–406 to provide a fluid path between the fluidic port 430 and the channel 462 defined in the seventh layer 407. During a slurry packing process, a via 426A defined in the second layer 402 communicates slurry from the slurry inlet port 426 to an elongate channel 438 defined in the third layer 403. Preferably, particulate material deposited by slurry packing fills a first common channel 442 and at least a portion of a further upstream channel 438. The second layer 402 further defines eight sample channels 435A–435H, each having an enlarged region 434A–434H, respectively. Each enlarged region 434A–434H is aligned with one of the eight corresponding sample inlet ports 428A–428H defined in the first layer 401.

The third layer 403 defines an elongate channel 438 along with eight sample vias 436A–436H, which are aligned with the small ends of the sample channels 435A–435H. The fourth layer 404 defines eight sample vias 444A–444H aligned with the vias 436A–436H in the third layer 403. A porous material or (sample) frit 440, which functions to retain stationary phase material in the separation channels 445A–445H but permits the passage of sample, is placed between the third and fourth layers 403, 404 and spans across the sample vias 444A–444H in the fourth layer 404. Although various frit materials may be used, the frit 440 (along with frits 450, 451 within the device 400) is preferably constructed from a permeable membrane such as, for example, 1-mil (25 microns) thickness Celgard 2500 polypropylene membrane (55% porosity, 0.209×0.054 micron pore size, Celgard Inc., Charlotte, N.C.). As described in more detail below, Applicants have obtained favorable results using this specific frit material, without noticeable wicking or lateral flow within the frit, despite using a single strip of the frit membrane to serve multiple adjacent separation channels 445A–445H containing stationary phase material. As a less-preferred alternative to the single porous frit 440, multiple discrete frits (not shown) may be substituted, and various porous material types and thicknesses may be used depending on the stationary phase material to be retained. The fourth layer 404 further defines a manifold channel 442 that provides fluid communication with the separation channels 445A–445H defined in the fifth layer 405 and the elongate channel 438 defined in the third layer 403. The separation channels 445A–445H preferably have a width of about 40 mils (1 mm) or less.

The sixth layer 406 defines a solvent channel 446 that receives a second mobile phase solvent and transports the same to the slit 452 (defined in the seventh layer 407), which facilitates mixing of the two solvents in the channel 464 downstream of the slit 452. Further defined in the sixth layer 406 are a first set of eight vias 448A–448H (for admitting mixed mobile phase solvents to the upstream end of the separation channels 445A–445H and the stationary phase material contained therein), and a second set of eight vias 449A–449H at the downstream end of the same channels 445A–445H for receiving mobile phase solvent and sample. Two frits 450, 451 are inserted between the sixth and the seventh layers 406, 407. The first (mobile phase solvent) frit 450 is placed immediately above the first set of eight vias 448A–448H, while the second (mobile phase+sample) frit 451 is placed immediately above the second set of eight vias 449A–449H and below a similar set of eight vias 460A–460H defined in the seventh layer 407. The seventh layer 407 defines a channel segment 458, two medium forked channel segments 468, and eight vias 454A–445H for communicating mobile phase solvent through the frit 450 and the vias 448A–448H to the separation channels 445A–445H defined in the fifth layer 405 and containing stationary phase material. The seventh layer 407 further defines a transverse manifold channel 462—that receives mobile phase solvent and sample following separation, and that receives solvent (separated from slurry) during column packing—for routing fluids through vias 430A to the fluidic exit port 430. The eighth layer 408 defines a mixing channel 464, one large forked channel segment 468, and four small forked channel segments 466. The eighth layer 408 further defines eight parallel channel segments 470A–470H downstream of the frit 451 for receiving (mobile phase) solvent and sample (during separation) or solvent (separated from slurry during column packing), and for transporting such fluid(s) to the manifold channel 462 defined in the seventh layer 407. The ninth layer 409 serves as a cover for the channel structures defined in the eighth layer 408.

FIG. 14B is a top view of the assembled device 400 of FIG. 14A. As is evident from FIG. 14B, the device 400 contains several regions where microfluidic channel structures overlap. The presence of microfluidic channel structures generally, but more particularly overlapping microfluidic channel structures, complicates the difficulty of adhesivelessly bonding the device layers 401–409, since these structures are prone to collapse if the device layers 401–409 are subjected to unduly high temperatures, high pressures, and/or long periods of sustained maximum temperature. If pressure is applied to stencil-based adhesiveless polyolefin device layers having overlapping channels during the heating step, the pressure should preferably be kept below about 10 psi (70 kPa), more preferably below about 5 psi (35 kPa), and even more preferably below about 1 psi (7 kPa). Using other polymers, higher pressures may be used, but it is anticipated that preferably pressures will remain below 100 psi (700 kPa). The presence of many device layers (here, nine device layers 401–409) is another complicating factor, since it is desirable to ensure that all of the layers 401–409 are bonded completely without overheating the outermost layers. An additional complicating factor is the presence of several frits 440, 450, 451 in the device 400. These frits 440, 450, 451 cause the device 400 to have regions of non-uniform thickness, since the frits 440, 450, 451 do not span the entire area of the device 400. These regions of non-uniform thickness render it more difficult to apply uniform pressure across an entire surface of the device 400. Also, since it is desirable to prevent wicking or lateral flow within any of the frits 440, 450, 451, a preferred bonding method should cause the frits 440, 450, 451 to be integrally bonded with the surrounding layers at all regions except along the adjacent vias (e.g., along vias 436A–436H, 444A–444H, 448A–448H, 454A–454H, 449A–449H, 460A–460H), where the frits should remain porous to permit fluid flow therethrough. Further, the highest temperature attained by the frits during heating step should remain below the frit material melting point to ensure that the pores remain fluid-permeable. All of these factors contribute to the difficulty of manufacturing a complex microfluidic separation device 400 with an adhesiveless bonding process.

Preferred Methods for Bonding Adhesiveless, Substantially Metal-free Device Layers According to a preferred method, a fluidic microstructure is formed by stacking a plurality of adhesiveless, substantially metal-free device layers—including a first cover layer, a second cover layer, and at least one channel-defining stencil layer disposed between the cover layers—between platens, and then controllably heating the device layers. The device layers are controllably heated according to a heating profile adapted to form a substantially sealed microfluidic device yet avoid channel collapse. During the heating step, the platens preferably maintain intimate contact with the outer (i.e., cover) layers surrounding the other device layers, including one or more stencil layer(s).

FIG. 1A shows two platens 16, 17 maintaining intimate contact with the outer surfaces of the outermost layers of multiple stacked polymeric device layers 10, including at least one channel-defining stencil layer. Following a controlled heating step, the platens 16, 17 may be removed from the bonded layers 10. The platens 16, 17 preferably have substantially flat and smooth surfaces to promote intimate contact with the outer device layers, are inert, and are characterized by a relatively high melting point. For example, platens may be advantageously fabricated using various types of commercially available glass, including borosilicate glass, although other materials may be used.

Applicants have occasionally observed the formation of irregularly shaped, rough, and slightly opaque regions along the outer surfaces of adhesiveless devices fabricated using methods according to the present invention. It is believed that these regions correspond to locations where intimate contact between the outer layers of the device and the platens was not maintained during the heating step. These regions are thus termed "lack of contact" or "LOC" regions. Potential causes of LOC regions may include the formation of steam from moisture present during the heating step. LOC regions are preferably avoided because it is believed that they may detrimentally affect bonding between the outermost layers, and/or cause undesirable distortion of internal features. LOC regions are further undesirable in situations where it would be desirable to use optical detection techniques with the resulting device, since LOC regions exhibit unpredictable optical properties. Applicants have observed that lower occurrences of LOC regions seem to correspond to: (1) elevated pressures, and/or (2) longer heating durations; however, care should be exercised in altering these parameters to avoid other problems such as channel collapse. It is believed that the incidence of LOC regions may be further reduced by paying careful attention to the flatness of the platens and device layers, promoting even pressure distribution across the device(s), and ensuring that device layers are substantially free of moisture. Notably, Applicants have successfully produced large numbers of adhesiveless microfluidic device substantially free of visible LOC pockets according to methods disclosed herein.

In one embodiment, device layers are stacked between platens, and the stacked device layers do not extend laterally beyond the edges of the platens. For example, FIG. 2C illustrates multiple device layers 20 disposed between platens 26, 27 in a jig assembly 19, with the device layers 20 extending up to but not beyond the edges of the platens 26, 27. Preferably, during the stacking step the device layers 20 are carefully aligned, and this alignment may be advantageously maintained by locally melting one or more layers together, preferably along one or more outer edges of the stacked device layers 20. Alternatively, localized heating of the device layer 20 by laser welding or ultrasonic welding may be used.

Referring back to FIG. 1A, if the platens 16, 17 and device layers 10 are disposed horizontally, then when the upper platen 16 is placed atop the stacked device layers 10, the upper platen 16 exerts a compressive force on the device layers 10 due to the weight of the platen 16. As will be recognized by one skilled in the art, the mass of the upper platen 16 may be selected to provide a desired compressive force. However, altering the mass of the platens 16, 17 will also tend to affect the thermal response of the system. Thus, while not essential to practicing the invention, a preferred fabrication method includes the application of a further compressive force to the stacked platens 16, 17 and device layers 10 during the heating step. FIG. 1B provides arrows illustrating the direction in which compressive force is applied through the platens 16, 17 to the stacked device layers 10. The compressive force is preferably applied fairly evenly across the device layers 10. Distribution of this force may be affected by both the positioning of the device layers 10 between the platens 16, 17 and the particular application of compressive force. For example, if it is desired to produce only one stacked microfluidic device between two platens, then the single stack of device layers 10 are preferably disposed in a substantially central position between the platens. If it is desired to produce multiple microfluidic devices from multiple discrete stacks of device layers disposed between two platens, then the multiple stacks of device layers may be disposed in a symmetrical pattern relative to the center of each platen 16, 17.

One method of applying compressive force includes adding one or more weights to the upper platen 16. For example, FIG. 1C illustrates device layers 10 compressed between an upper platen 16 and a lower platen 17, with a weight 18 applied to the upper platen 16. Preferably, the weight 18 is placed in a substantially central position above the upper platen 16.

As an alternative to using weights, a stack of device layers may be compressed using one or more springs, such as by using a jig disposed around the platens. If a jig is used to maintain compression between the platens and the microfluidic device layers, then the jig-platen-device assembly may be oriented vertically during the heating step if desired. If multiple springs are employed, then preferably an equal force is provided by each spring and the force from each spring is distributed evenly across the platens. One advantage of using springs to apply compressive force during the heating step is that they provide relatively constant compressive force in spite of possible differential thermal expansion between the jig members 30, 32 and the bolts 36.

FIG. 2A illustrates a compressive jig assembly 19 that may be used to permanently bond adhesiveless polymeric device layers according to the present invention. Multiple device layers forming an array 20 are placed between a first platen 26 and a second platen 27. One or more discrete device layer stacks may be substituted for the array 20 if desired. A further view of the array 20 is provided in FIG. 2E. Notably, the array 20 may be scored or perforated along cuts 22 to aid in separating the array 20 into multiple (e.g., nine) discrete devices following the heating step, each device having channels 24 and fluidic ports 23. It is believed that the cuts 22 may further assist in reducing the incidence of encapsulated air/gas bubbles between device layers. Joined or connecting regions 21 may be provided. Referring back to FIG. 2A, the platens 26, 27 and array 20 of stacked device layers are placed between a first and a second outer jig member 30, 32. The second jig member 32 includes a lip 33 defining a recess 35. The platens 26, 27 are sized to fit, preferably snugly, within the recess 35 to prevent lateral movement of the platens 26, 27 when the compressive jig assembly 19 is assembled, as shown in FIGS. 2B–2C. Aligned holes 31, 34 are provided in the first and the second jig member 30, 32 to accept bolts 36. Preferably, the holes 31 in the first jig member 30 are sized to permit the threaded portions of bolts 36 to pass and are not tapped, and the holes 34 in the second jig member 32 are tapped to engage the bolts 36.

The platens 26, 27 and the stacked multi-layer microfluidic device array 20 may be fitted into the recess 35 defined in the second jig member 32, preferably with a portion of the first platen 26 extending above the lip 33 in the second jig member 32 to permit the stacked platens 26, 27 and device array 20 to be compressed with the first jig member 30. At each corner of the assembly 19, a spring 38 is engaged to the upper jig member 30 with a bolt 36 and washer 37, the bolt threads extending into a tapped hole 34 in the lower jig member 32. Tightening the bolt 36 compresses the spring 38, ultimately applying a compressive force to the multi-layer array 20 through the jig members 30, 32 and the platens 26, 27. The magnitude of the compressive force to be applied may be varied by selecting appropriate springs and adjusting the deflection of those springs. Preferably, equal compressive forces are applied at each corner of the assembly 19 to promote even pressure distribution across the multi-layer device array 20. Further, the jig members 30, 32 are preferably sized to prevent deformation or warping under compressive load. The jig members 30, 32 may be advantageously formed of a metal such as aluminum or steel.

It is believed that the preferred magnitude of compressive forces applied to a stack of device layers according to bonding methods described is relatively low compared to pressures used with conventional methods (e.g., as disclosed by the Moles reference and the Gumm reference). For example, using polyolefins, preferable compressive pressures are below about 10 psi (70 kPa), more preferably below about 5 psi (35 kPa), more preferably below about 2 psi (14 kPa), and, in some cases, more preferably between about 0.25–0.50 psi (1.72–3.45 kPa). Using other polymers, higher pressures may be used, but it is anticipated that preferably pressures will remain below 100 psi (700 kPa). These pressure values refer to the force applied per unit area of device layers sandwiched between the platens. The compressive force may be applied using weights, springs, pistons, or any suitable apparatus. A potential advantage of using an externally controlled compression means, such as a piston/cylinder apparatus, is that the compressive force applied to the device layers may be controllably varied during the heating step, during a cooling step, or any portions thereof.

Applicants have permanently bonded a large number of adhesiveless multi-layer devices having desired dimensions by selecting particular ranges of values for different process parameters. The values for several parameters—including the temperature attained by the device layers, the period that the device layers are maintained at a desired temperature, the pressure applied to the device layers—may be varied within certain ranges and yet still achieve favorable results (namely, devices with high inter-layer bond strength and collapse-free microstructures). Notably, these parameters appear to be functionally related. For example, within discrete ranges, it appears that comparable positive results may be obtained by heating for a longer time at a lower pressure or by heating for a shorter time at a higher pressure. Care must be exercised when varying bonding parameters, however, since structures are prone to collapse if the device layers are subjected to unduly high temperatures, high pressures, and/or long periods of sustained maximum temperature.

Using polyolefins, Applicants have obtained favorable results using temperatures between about 151–156° C. for periods between about 0.75 to 24 hours, usually accompanied by application of a slight compressive force between about 0.25–1 psi (1.7–7 kPa). Generally, within these ranges Applicants have obtained similar results by applying lower temperatures for a longer period of time or by applying higher temperatures for a shorter period of time. Such heating may be performed using any suitable industrial oven capable of even heating within a tightly controlled temperature range. Applying temperatures significantly higher than 156° C. to polypropylene device layers—perhaps temperatures as low as 158–160° C.—seems to detrimentally affect the integrity of microstructures, as the device layers appear to melt and flow within this threshold.

Preferably, the polymer device layers are controllably heated during the heating step to within ±10 percent of the Celsius differential scanning calorimetric ("DSC") melting point of the polymer, more preferably to within ±5 percent of the Celsius DSC melting point, and more preferably to within ±2 percent of the Celsius DSC melting point. These narrow ranges are desirable to achieve substantially sealed microfluidic devices wherein the upper surface of each channel remains distinct from its respective lower channel surface (i.e., maintaining the integrity of channel structures). In other words, sufficiently high temperatures should be attained to promote high-strength bonds between device layers, yet temperatures should be limited to avoid excessive polymer flow that would result in microfluidic channel collapse.

Following the heating step, the (bound) device layers are cooled to ambient temperature. Applicants have found that the rate at which the bound layers are cooled affects the material properties of the resulting device. It is believed that this is due to the resulting degree of crystallinity of the polymer. As a result, if it is desired to obtain devices with relatively uniform material properties, then the device layers should be cooled using a consistent cooling profile.

Preferably, control of the heating and/or cooling steps is aided by the use of one or more temperature sensors. Such sensor(s) preferably sense the temperature of the platens or device layers. A sensor is preferably placed in intimate contact with a platen, a weight touching a platen, or any other suitable location in direct or indirect thermal contact with the device layers. Preferably, feedback control of the heating and/or cooling steps is provided. A central controller may be provided to assist with temperature control, pressure control, and/or any other suitable automation step.

The heating step may be performed by various heating processes, including thermoelectric heating, resistive heating, convective heating, and conductive heating. Device layers may be heated along with platens within an oven or other enclosure. Alternatively, the heating step may be performed by elevating the temperature of the platens rather than the environment common to the device layers and platens.

Applicants have observed that humidity can affect adhesiveless bonding using methods described herein. Specifically, it has been observed that high humidity is detrimental. It is believed that the presence of adsorbed and/or absorbed water during the heating step causes the formation of steam, which does not allow the intimate contact between layers that is required for optimal bonding. Accordingly, it is preferred to dry the adhesiveless polymer layers before and/or during the heating step. This can be accomplished by placing the device layers, preferably along with the heating equipment, in a dehumidified environment such as an enclosure with a dehumidifier. Elevated ambient temperatures in the enclosure are believed to assist with the drying process. For example, in a preferred method, device layers are placed in an environment having a relative humidity of no more than about 30 percent, more preferably a relative humidity of no more than about 25 percent, and having a temperature of at least about 90° F., for a period of at least about 12 hours prior to the controlled heating (bonding) step. Additionally, the heating (bonding) equipment is preferably maintained in an environment having a relative humidity of no more than about 30 percent.

In another embodiment, thin thermally conducting layers (e.g., metallic foil) are placed between insulating platens and the stacked device layers. An illustrative apparatus is provided in FIG. 11. Multiple stacked adhesiveless polymeric layers 305, including at least one channel-containing stencil layer, are placed between two thin thermally conducting layers 303, 304, which are themselves placed between two thermally insulating platens 301, 302 to form a stack 300. The stack 300 is heated, such as within an industrial oven, to permanently bond the polymer layers to form a microfluidic device. Preferably, the adhesiveless polymer layers are also subjected to a compressive force. The entire stack 300 may be compressed, such as by adding a weight 308 to the upper platen during the heating step. Additionally, or possibly alternatively, the sub-stack of polymeric layers 305 may be forcibly compressed prior to the heating step. When thin device layers are used to define microfluidic channel structures, however, care should be taken to avoid compressing the polymeric layers 305 to the point of collapsing or otherwise damaging the channel structures.

If desired, multiple microfluidic devices may be fabricated between a single set of thermally insulating platens if appropriate thin conducting layers are used to segregate adjacent sub-stacks of adhesiveless polymer layers. For example, FIG. 12 illustrates an apparatus useful for producing several microfluidic devices simultaneously. There, three sub-stacks 327–329 of multiple adhesiveless polymeric layers, each sub-stack defining at least one microfluidic channel structure, are placed between two substantially flat, thermally insulating platens 321, 322, with each polymeric sub-stack 327–329 being separated from one another and from the platens 321, 322 by thin thermally conductive (e.g., metal foil) layers 323–326 to form a stack 320. While various platen materials may be used, the platens 321, 322 are preferably substantially rigid and flat, and should have a significantly higher melting temperature than the polymer layers to be bonded between the platens 321, 322. One preferred platen material is glass. Compressive force may be applied to the stack 330 such as by positioning a weight 330 atop the upper platen 321. The stack 320 is heated, such as within an industrial oven, to permanently bond the substacks 327–329 of polymer layers to yield three discrete, substantially sealed microfluidic devices.

While the exact reason(s) why the foil layers aid the adhesiveless bonding process are not completely understood, it is believed that the foil layers promote a more even temperature distribution across the width of the device layers. Preferable materials for the thin thermally conducting layers include carbon steel, stainless steel, aluminum, and copper.

Examples of different combinations for bonding multi-layer, stencil-based microfluidic devices (similar to the device 400 illustrated in FIGS. 14A–14B and measuring about 3.5×5.5×0.125 inch or 8.9×14×0.32 cm) made with adhesiveless, substantially metal-free unoriented polypropylene layers sandwiched between 3.75×6×0.25 inches (9.5× 15.2×0.64 cm) glass insulating platens and between thermally conducting 3.5×5.5×0.003 inch (8.9×14×0.008 cm) layers of carbon steel foil are provided in the following table:

| Temp [° C.] | Time [hrs] | Pressure [psi] | Vacuum pre-treatment? | Grade |
| --- | --- | --- | --- | --- |
| 154 | 1.0 | 0.25 | no | Fail |
| 154 | 4.0 | 0.25 | no | Pass |
| 154 | 3.0 | 0.25 | yes | Pass |
| 154 | 2.0 | 0.30 | no | Pass |
| 156 | 1.5 | 0.48 | no | Pass |
| 158 | 2.0 | 0.48 | no | Fail |
| 146 | 15.0 | 0.66 | no | Pass |
| 152 | 4.0 | 0.66 | no | Pass |
| 152 | 4.0 | 0.98 | no | Pass |

In the table, "time" refers to heating time in an industrial oven. "Pressure" refers to the pressure applied to the device layers by weighting the upper insulating platen of each stack. "Vacuum pre-treatment" refers to an optional step of inserting the sub-stack of polymeric layers into a vacuum chamber and applying sub-atmospheric pressure to the sub-stack for a period of at least 30 minutes. Only devices that exhibited complete and permanent bonding between layers coupled with no collapsed microstructures and no lack of contact or "LOC" regions were assigned the grade of "pass". However, complete bonding through frit materials was not deemed a necessary criterion to obtain a passing grade.

It is contemplated that various other combinations of adhesiveless bonding parameters may be used for polypropylene and for other polymers. It is expected that operative parameter ranges that work for one material may not work for another material.

The optimal bonding parameters for any given microfluidic device design seems to depend on several factors, including: (1) the type of material used; (2) the number of layers in the device (e.g., fewer layers appear to require less time); (3) the dimensions of the device (e.g., larger devices appear to require more time); and (4) whether the device includes a porous frit material (which, if present, tends to increase the time required to achieve complete bonding around and/or through the frit material). If it is desired to bond a large number of devices simultaneously in a single oven, then the oven should be selected with sufficient heating capability to provide rapid and uniform temperature control.

A preferred heating profile for one or more microfluidic devices according to (or substantially similar to) the design of the device 400 illustrated in FIGS. 14A–14B and fabricated with polypropylene device layers—particularly when it is desired to achieve complete incorporation of porous frit materials—includes a first heating step at 152° C. for about 5 hours, followed by a first cooling step with a forced flow of ambient air for at least about 30 minutes, followed by a second heating step at 146° C. for about 15 hours, finally followed by a second cooling step identical to the first cooling step. During each heating step, a pressure of about 0.37 psi (2.55 kPa) is applied to the one or more microfluidic devices. A thermally conducting layer (e.g., metallic foil) is placed against each outer face of the microfluidic device(s), with one thermally insulating layer (e.g., glass) each disposed at the top and bottom of the stack. Utilizing such a process, the various device layers are completely and permanently bonded together, and porous frit materials of substantially similar surface energy to the surrounding device layers are incorporated completely into the device except along voids such as vias adjacent to the porous frit material.

FIG. 15 illustrates a cross-sectional view of at least a portion 500 of a stencil-based adhesiveless microfluidic device. Although FIG. 15 provides only a single channel 505 and simple three-layer structure, one skilled in the art will readily recognize that alternative channel configurations may be used, and that the illustrated channel structure may be taken to represent either a simple stand-alone channel or a portion of a more complex microstructure provided deep within a multi-layer device. The channel 505 is a microfluidic channel bounded laterally by the stencil layer 504, and bounded from above and below by device layers 501, 502. One or both of the device layers 501, 502 adjacent to the stencil layer 505 may be cover layers, other stencil layers, or intermediate layers containing through-holes permitting fluid communication between non-adjacent stencil layers. The upper device layer 501 defines the upper channel surface 506 and the lower device layer 502 defines the lower channel surface 508. All three layers 501, 502, 505 are adhesiveless, substantially metal-free polymer layers. If care is not exercised when bonding the device layers 501, 502, 505, then either of two results is likely. One likely result, often resulting from insufficient heating and/or intimate contact between layers, is poor bonding between layers (along boundaries between adjacent layers 501, 504 and 502, 504), thus failing to provide a substantially sealed microstructure (e.g., channel 505) capable of withstanding desirable high fluid pressures. The other likely result, often resulting from excessive heating and/or application of pressure, is collapse of the channel 505, wherein the upper channel surface 506 contacts the lower channel surface 508.

Adhesiveless microfluidic devices may be bonded between platens that are heated directly (e.g., with integral electric resistance elements or similar heating means). For example, a clamshell-type assembly having an upper and a lower platen, and preferably having highly polished and durable (e.g., anodized aluminum) surfaces and means for varying the compressive pressure to be applied by the platens, may be provided to facilitate adhesiveless bonding. A preferred bonding process would heat substantially clear adhesiveless polymer layers, such as polyolefin layers, of a microfluidic device to a sufficient temperature to permit interdiffusion, but not to so high a temperature to cause liquefaction of the material and resulting collapse of microstructures defined by the layers.

FIG. 16 is a schematic of a heated platen system 600 permitting control of various bonding parameters. A bonding apparatus 601 includes a stationary upper platen 602 suspended on peripheral support columns 608 and a vertically translatable lower platen 604 that is laterally constrained by the columns 608. Multiple device layers 605 to be bonded are placed between the platens 602, 604. Vertical translation of the lower platen is facilitated by a piston-cylinder apparatus such as a pneumatic cylinder 614 (e.g., such as pneumatic cylinders commercially available from Bimba Manufacturing Co., Monee, Ill.). The feed of compressed gas from a gas source 610 to the cylinder 614 is controlled by a control valve, more preferably a proportional pressure controller 612. Each platen has at least one, and preferably multiple, thermoelectric modules 620 (e.g., thermoelectric/Peltier modules commercially available from TE Technology, Inc., Traverse City, Mo.) preferably capable of both heating and cooling the platens 602, 604. Each thermoelectric module 620 has an associated heat sink 624 and cooling fan 626. At least one power supply 622 handles the electric requirements of the thermoelectric modules 620. One or more temperature sensors 632, 634, such as thermocouples, thermistors, or resistance temperature devices, are provided to facilitate temperature control, preferably using a feedback loop. While the temperature sensors 632, 634 are illustrated in thermal communication with the platens 602, 604, they may also be placed in direct thermal communication with the device layers or in another suitable location. Preferably, a system controller 630 is provided to control the system 600. While various types of conventional controllers may be used, a preferred controller 630 is microprocessor-based to execute a user-defined set of instructions. The system controller 630 receives signals from the temperature sensors 632, 634 and provides appropriate signals to the power supply 622, pressure controller 612, and fans 626. One advantage of the system 600 is that it permits precise control of device layer heating and cooling, and also permits fine control of the pressure applied to the device layers 605. The pressure applied to the device layers 605 can be varied during any portion of the heating and/or cooling steps if desired.

Incorporation of Various Materials into Adhesiveless Stencil-based Microstructures In certain embodiments, utilitarian objects of various types may be added to a stencil-based adhesiveless microstructure. Representative objects include, for example, capillary tubes, frits, electrospray needles, and wires or electrodes. Other objects include filling materials, including but not limited to beads, granules, monoliths, porous plugs and other filter or catalyst materials. Certain objects may be only partially incorporated into a microfluidic device, such as, for example, a wire/electrode, or an electrospray needle or similar tubular nozzle may protrude from a device. With certain objects it is desirable to ensure sealing engagement with a surrounding microstructure. For example, sealing engagement is preferably provided between a microstructure and an encapsulated capillary tube, electrospray needle, porous plug, or filter material to promote fluid flow through, rather than around, the object. Sealing engagement around the encapsulated object may be aided by coating the object with a hot-melt or other polymeric material prior to the heating step so as to fill any potential voids between the object and an adjacent microstructure.

With other objects (such as, for example, beads, granules, catalyst materials, or wire-type electrodes) sealing engagement between the object and the associated microstructure is either unnecessary or undesirable. In a preferred embodiment, filling materials such as beads or granules may be packed within a microstructure. Such packing is advantageously performed at elevated pressures, and may be aided by the addition of at least one porous frit to the microstructure to restrain the packing material.

Selectively Preventing Permanent Bonding Between Layers at Specific Regions

In certain embodiments, it is desirable to provide a multi-layer microstructure that is substantially sealed without using adhesives, but that also has specific regions wherein adjacent layers are not permanently bonded together. In these unbonded regions, one or more layers may be advantageously flexed or deformed, such as may be desirable to provide fluid control utility. For example, a deformable region may be used to selectively permit fluid passage through one segment of a fluidic circuit.

Several methods exist for preventing permanent bonds from forming in specific regions between layers of a microfluidic device formed according to the present invention. One preferred method for ensuring that a permanent bond does not result between two adjacent layers takes advantage of the susceptibility of certain materials to degradation. In one embodiment, a degradable material is placed between layers of the device in one or more specific regions before the heating step in a direct bonding process. Following the heating step, the adjacent device layers are permanently bonded along all contacting surfaces. Insertion of a degradable material between layers of the device in one or more specific regions prevents inter-layer contact, and thus permanent bonding between adjacent device layers, in those regions. The degradable material may be subsequently degraded and preferably removed from the device, resulting in specific unbonded regions within a substantially sealed microstructure.

As noted previously, the term "degradable material" in this context refers to a material that may be degraded without destroying or otherwise impairing the use of the surrounding microstructure. Thus, selection of a particular degradable material is preferably performed with consideration to the material of the associated microstructure, such that the process of degrading the degradable material does not detrimentally affect the microstructure. Numerous degradable materials may be used. Where the microstructure is fabricated from polypropylene materials, examples of specific degradable materials that may be used to prevent permanent bonding between layers in localized regions include: [a] vinyl films, such as 2-mil (50 micron) thickness Avery Graphics A8 Opaque (Avery Dennison, Brea, Calif.) vinyl film with an acrylic adhesive on one side; and [b] acrylic transfer adhesives, such as 3M Adhesive Transfer Tape No. 9447 (3M, St. Paul, Minn.). Both exemplary classes of materials (e.g., vinyl films and acrylic transfer adhesives) may be readily degraded by solvents such as dichloromethane (DCM) that do not attack polypropylene. For example, prolonged contact with DCM (e.g., for a period of approximately 24 hours) completely dissolves Avery Graphics A8 vinyl film, while the same solvent degrades 3M 9447 acrylic adhesive into a gooey gel that may be readily flushed out of a thermally bonded adhesiveless polypropylene microstructure. To aid in patterning a degradable material onto one or more surfaces, conventional methods such as silk-screening or other patterning through a mask may be employed.

Another method for preventing permanent bonding between layers in specific regions of a thermally bonded device involves the addition of a substantially inert substance such as a grease between layers in such regions. A preferred substance for such use is a fluorinated grease, such as DuPont Krytox® GPL 206 or Krytox® LVP grease (E.I. DuPont de Nemours and Co., Wilmington, Del.). These PTFE-thickened fluorinated alkane greases are thermally stable and chemically inert, thus making them suitable to prevent bonding between device layers. Additionally, since such greases are insoluble in and resist degradation by most aggressive chemicals, they may remain within the resulting microstructure without necessarily contaminating a fluidic sample contained therein. An inert grease may be placed in one or more selected locations between adjacent layers using any suitable technique, such as manual or automated dabbing. A target layer for receiving inert grease in specific regions may be overlaid with mask layer to aid in precise placement of the grease.

Yet another method for preventing permanent bonding between layers in specific regions of a thermally bonded device involves localized coating of one or more layers with an inert material to resist inter-layer bonding in such regions. For example, polytetrafluoroethylene (PTFE) may be locally deposited or patterned onto a surface of a polypropylene layer. Preferred deposition methods include the spraying of molten PTFE onto a polypropylene surface. Prior to the deposition step, the target polypropylene surface optionally may be locally surface treated using techniques such as corona discharge or ozone treatment in such regions to aid in adhering the PTFE to the polypropylene. A mask layer may be advantageously used to aid in the deposition or optional surface treatment steps to prevent unwanted modification in the remaining regions of the target layer.

EXAMPLES

The following Examples describe in detail several preferred embodiments of the present invention, and are intended to be illustrative, not limiting.

Example 1

Several copies of a square adhesiveless microfluidic channel-containing device were constructed with three device layers 51–53, with edge lengths of about 2.5 inches (6.4 cm). Referring to FIGS. 3A–3B, in each device the first (cover) layer 51 defined an inlet port 55 and an outlet port 56 for each channel 57. Eight channels 57, each 40 mils (1 mm) wide, were cut into and through the entire thickness of the central stencil layer 52. The third (cover) layer 53 served to enclose the channels 57 from the bottom. Each layer 51–53 defined two alignment holes 58, 59 to aid in aligning the layers 51–53 when stacking atop an alignment jig with raised pegs (not shown). The three layers 51–53 were each formed of 7.5 mil (188 micron) thickness unoriented "Clear Tear-Seal" polypropylene (American Profol, Cedar Rapids, Iowa) and stacked together. No adhesives or metallic bonding agents were used.

In one batch, the channels 57 were cut with a computer-controlled laser cutter. Multiple (i.e., four) stacks of layers 51–53 were positioned symmetrically between two rectangular 0.25 inch (6.4 mm) thick glass platens (such as the platens 16, 17 shown in FIG. 1C) with weight applied to the upper platen to apply a pressure of 0.26 psi (1.79 kPa) to the layered stacks. The weighted platens and device layers were placed on a rack within an industrial oven and heated for a period of about 5 hours at a temperature of 154° C. Following the heating step, the weighted platens and device layers were removed from the oven to cool at room temperature. The platens were gently pried away from each stack of device layers, which were permanently bonded together to form a microfluidic device 50. Dimensional integrity of the channels 57 and ports 55, 57 were maintained, with no signs of channel collapse. The resulting devices 50 appeared translucent in all areas outside of the channels 57 and ports 55, 56; the channels 57 and ports 55, 56 were cloudy in appearance but still transmitted light. Fluid was circulated under pressure through the channels 57 in the resulting device 50, and no leaks were observed.

Example 2

Another batch of devices 50 identical in appearance to those described in Example 1 was prepared. The only difference in preparing the device layers 51–53 before stacking was that the channels 57 were cut using a plotter that was modified to manipulate a cutting blade. Nine aligned identical stacks of layers 51–53 were prepared and tack-welded at two locations each using a laser to provide a localized weak bond between layers. This welding step locally heated the material to approximately its melting point but did not burn or remove any material. This localized welding was performed to prevent slippage between layers 51–53 when placed within a compression jig.

The nine stacks were placed symmetrically, in three rows of three stacks each, between glass platens in a compression jig according to FIGS. 2A–2D. In this example, the compression springs 38 were each approximately ⅝ inch (16 mm) in length, 0.24 inch (6.1 mm) in diameter, and had a spring rate of about 28 pounds/inch (5.0 kg/cm). Each of the bolts 36 were size #10 with 32 threads/inch (12.6 threads/cm). A torque wrench was used to tighten the bolts 36 and compress the springs 38; each bolt was torqued to a value of about 3 inch-pounds (3.5 kg-cm) to transmit a roughly equal compressive force across the area of the platens 26, 27. Thereafter, the entire compression assembly was placed into an industrial oven and heated at a temperature of 156° C. for a period of approximately 1.5 hours. The entire assembly was then removed from the oven and allowed to cool at room temperature. After cooling, the platens were removed and nine permanently bonded eight-channel microfluidic devices 50 resulted with results substantially the same to those described in Example 1.

Example 3

Multiple copies of a microfluidic channel-containing device were constructed using five device layers 71–75. As shown in FIGS. 4A–4B, three stencil layers 72–74 were sandwiched between a first and a second cover layer 71, 75. The first layer 71 defined multiple inlet and outlet ports 77, 78. Eight channels 80, each approximately 40 mils (1 mm) wide were cut into and through the entire thickness of the second (stencil) layer 72, along with vias 81 and 82 for communicating with channels 84, 88 in the third and fourth layers 73, 74. The third layer 84 and the fourth layer 88 were stencil layers each defining eight channels 84, 88, with the third layer additionally defining vias 85, 86 for communicating with the channels 88. The channels 80, 84, 88 were all slightly offset from one another, as clearly depicted in FIG. 4B. The fifth layer 75 served as a base for sealing the channels 88 defined in the fourth layer 74. All five layers 71–75 were formed of 7.5 mil (188 micron) thickness unoriented "Clear Tear-Seal" polypropylene (American Profol, Cedar Rapids, Iowa) and stacked together. No adhesives were used between the device layers. All channels, ports, and vias were cut through the applicable layers using a computer-controlled laser cutter.

Multiple aligned stacks of device layers 71–75 were prepared and each 'tack welded' to provide a localized weak bond using a laser. This localized welding was performed to prevent slippage between layers and potential misalignment when the layered stacks were sandwiched between two rectangular 0.25 inch (6.4 mm) thick glass platens. As before, a weight was added to the upper platen to apply a pressure of about 0.26 psi (1.79 kPa) to the layered stacks. The weighted platens and device layers were placed on a rack within an industrial oven and heated for a period of about 5 hours at a temperature of 154° C. The resulting devices were permanently bonded with results substantially the same as described in Example 1.

Example 4

An adhesiveless microfluidic mixing reactor for mixing two fluid streams was constructed. Referring to FIGS. 5A–5B, the first layer 101 defined two inlet ports 107, 108 and one outlet port 109. An elongated serpentine channel 112 having a nominal channel width of approximately 40 mils (1 mm) was cut into and through the entire thickness of stencil layer 102. The second layer 102 further defined a via 110 for communicating fluid between the first layer 101 and the third layer 103. The third layer 103 defined a further via 114 and a slit 103. The fourth stencil layer 104 defined a channel 115 permitting fluid communication between the via 114 and the slit 103. The fifth layer 105 provided a lower boundary to the channel 115 in the fourth layer. The five layers 101–105 were each formed of 7.5 mil (188 micron) thickness unoriented "Clear Tear-Seal" polypropylene (American Profol, Cedar Rapids, Iowa) and stacked together. No adhesives or metallic agents were used between or within the device layers 101–105. A computer-controlled laser cutter was used to cut the channels, ports, vias, and slit through the entire thickness of individual layers 101–104.

The five device layers 101–105 were carefully aligned as they were stacked, and the layers were locally tack welded in one point by laser heating. The resulting stack was placed between two 0.25 inch (6.4 mm) glass platens, to which weights added to the upper platen to apply a pressure of about 0.26 psi (1.79 kPa) to the stacked layers 101–105. The weighted platens and device stack were placed in a commercial oven and heated at 154° C. for a period of approximately 5 hours. Following removal of the platens, the resulting device 100 exhibited negligible dimensional variation and good channel integrity with no collapsed channels, and was substantially translucent outside of the channel regions. The channel regions appeared slightly cloudy in color, but still transmitted light.

The fluidic mixing device 100 was tested to demonstrate its functionality. In operation, two fluids were injected into the inlet ports 107, 108 of the device 100 using syringes. The first fluid traveled through the first inlet port 107 and immediately into the serpentine channel 112 below. The second fluid traveled through the second inlet port 108 and vias 110, 113 into the channel 115 defined in the fourth layer 104. From this channel 115, the second fluid flowed upward through the slit 113 to merge with the first fluid contained in the channel 112 in the second layer 112. Downstream of the slit 113, a layered interface between the two fluids resulted, with the first fluid layered atop the second fluid. The two fluids mixed rapidly downstream of the slit 113, then traveled through the length of the serpentine channel and exited the device 100 through the outlet port 109. No fluid leakage from the device 100 was observed.

Example 5

Multiple batches of three-layer adhesiveless microfluidic devices similar to the device 50 illustrated in FIGS. 3A–3B were constructed. The devices according to the present Example each included only six, rather than eight, channels with corresponding ports, but the overall design, material, and dimensions were otherwise identical to the device 50 described previously. Multiple three-layer stacks were arranged symmetrically on a first rectangular 0.25 inch (6.4 mm) thick glass platen and then covered with a second identical glass platen, upon which a weight was added to apply a pressure of 0.48 psi (3.31 kPa). The weighted platens and device layers were then heated in an industrial oven at a temperature of 156 C. Favorable results consistent with the previous examples—including permanent bonding between device layers with insignificant dimensional changes and good channel integrity—were obtained with heating periods as short as about 0.75 to 1 hour. When the devices were subsequently tested with a pressurized fluid, no leakage was observed.

Example 6

Multiple copies of an adhesiveless three-layer microfluidic device having six channels were constructed. The device was similar to the device 50 illustrated in FIGS. 3A–3B and described previously. However, the device according to this example had six channels between 30–60 mils (750–1500 microns) wide. A further difference was that each layer was constructed of 4.3 mil (108 micron) thickness "U'NOPP type PP108/PP98" cast (unoriented) polypropylene film (NOW Plastics, Springfield, Mass.), indicated by the supplier to have a crystalline melting range of 146° C. After alignment and stacking, the stacked layers were placed between glass platens to which a weight was added to apply a compressive force of about 0.25 psi to each stack. Two different batches were prepared using an industrial oven. In a first batch, the weighted platen-device-platen assembly was heated at 154° C. for a period of 5 hours and then allowed to cool at room temperature. In a second batch, the weighted platen-device-platen assembly was heated at 154° C. for a period of about 3 hours, then heated at 160° C. for a period of about 2 hours, and finally allowed to cool at room temperature. Devices prepared in both batches exhibited permanent bonding between device layers, no perceptible dimensional change, no channel collapse, and good channel integrity with no observed leakage upon introduction of pressurized fluid to the channels. Interestingly, in both batches the channels were substantially translucent, compared to the frosty white color observed with the previous material sourced from American Profol. However, the devices prepared in both batches had many visible irregular mottled regions along the outside surfaces. Portions of the surfaces were translucent, while the mottled regions were less so but would still transmit light.

Example 7

An adhesiveless microfluidic device having multiple encapsulated capillary tubes was constructed. Referring to FIGS. 6A–6B, the device 120 was constructed from seven square device layers (having an edge length of about 2.5 inches (6.4 cm)) of 7.5 mil (188 micron) thickness unoriented "Clear Tear-Seal" polypropylene (American Profol, Cedar Rapids, Iowa). The first layer 121 defined six inlet ports 130 and six outlet ports 131. The second through the sixth layers 122–126 were all identical stencil layers, each defining six channels 132 about 40 mils (1 mm) wide. When stacked together, the second through sixth layer 122–126 formed a total of six channels 132 having a channel height equal to the sum of the thicknesses of the second through sixth layers 122–126. The seventh layer 127 served to provide a lower boundary for the channels 136. The channels 132 and ports 130, 132 were cut through the various layers 121–126 using a computer-controlled laser cutter. During assembly, the second through seventh layers 127 were first carefully aligned and stacked together.

Micropipette graduated capillary tubes (Drummond Scientific Co., Broomall, Pa.) having an inner diameter of about 0.49 mm and an outer diameter of about 1 mm were each trimmed to a length of about 38 mm, leaving the 1–5 microliter graduated region intact. Each of the resulting capillary tube sections 128 were carefully wrapped with a strip of 4-mil (100 micron) thickness modified polyolefin thermoplastic, specifically, Thermo-Bond Film 845 (3M, St. Paul, Minn.). The wrapped capillary tube sections 128 were then placed into the channels 132, resulting in a relatively snug fit between the wrapping and the walls of the open channels 132. The length of the channels 132 was greater than that of the capillary tube sections 128. Following the insertion step, the first layer 121 was added to the stack to enclose the channels 132. Thereafter, the stacked layers 121–127 with wrapped capillary sections 128 were placed between two square glass platens, each with an edge length of about 4 inches (10 cm) and about 0.25 inch (6.4 mm) thick. A 3 pound (1.4 kg) weight was added to the upper platen to apply a compressive pressure of about 0.48 psi (3.31 kPa) to the stack, and the weighted assembly was then placed in an industrial oven and heated at about 154° C. for a period of 3 hours.

After cooling to room temperature, the platens were removed. The previously distinct device layers 121–127 were permanently bonded into a microfluidic device 120 with six embedded capillary tube sections 128. Outside of the channels 132, the device appeared translucent. Within the channels 132, the polyolefin thermoplastic appeared to be fused with the channel walls and the capillary sections 128. The graduated marks on the capillaries 128 remained visible. Fluid was circulated under pressure through the capillary sections 128 and ports 130, 131 in the resulting device 120, and no leakage between layers or around the capillaries 128 was observed.

Example 8

Multiple eight-layer adhesiveless microfluidic devices similar to the device 120 illustrated in FIGS. 6A–6B were constructed. The devices according to the present Example each included six, rather than five, intermediate stencil layers (all identical to stencil layer 122) and did not include embedded capillary tubes 128, but otherwise resembled the device 120. Each device layer was formed of 7.5 mil (188 micron) thickness unoriented "Clear Tear-Seal" polypropylene (American Profol, Cedar Rapids, Iowa) and stacked together. Six 40-mil (1 mm) wide channels in each of the six intermediate stencil layers were cut through each layer using a computer-controlled plotter modified to manipulate a cutting blade. The device layers were carefully aligned and stacked together without using adhesives. Multiple eight-layer stacks were arranged symmetrically on a first rectangular 0.25 inch (6.4 mm) thick glass platen and then covered with a second identical glass platen, upon which a weight was added to apply a pressure of 0.48 psi (3.31 kPa). The weighted platens and device layers were then heated in an industrial oven at a temperature of 156° C. for a period of about 1.5 hours. The resulting devices exhibited permanent bonding between device layers with insignificant dimensional changes and good channel integrity. When pressurized fluid was flowed through the resulting channels of the devices, no leakage was observed.

Example 9

An adhesiveless microfluidic device having an integral electrospray needle was constructed with three device layers 151–153. Referring to FIGS. 7A–7B, an inlet port 155 was cut into and through the first layer 151 using a computer-controlled laser cutter. The second stencil layer defined a channel 156 (approximately 40 mils (1 mm) wide) and a slit 157. No material was removed from the second layer by cutting the slit 157; rather, the layer 152 was locally cut or separated in this area using a cutting blade. The third layer 153 provided a lower boundary for the channel 156 and slit 157 defined in the second layer 152. To prepare for insertion of an electrospray needle 154, the second layer 153 was stacked atop the third layer 153.

An electrospray needle 154 was prepared using 7.5 mil (188 micron) metallic syringe tubing (McMaster-Carr Supply Co., Los Angeles, Calif.). After being cut to the desired length, the cut end of the needle 154 was polished and then coated with a thin layer of molten polypropylene created by heating a 7.5 mil (188 micron) thickness unoriented "Clear Tear-Seal" polypropylene (American Profol, Cedar Rapids, Iowa) film on a hot plate, taking care not to clog the hollow needle 154 during the coating step. The coated needle 154 was then placed into the slit 157 with one end located in the channel 154 and the other protruding outward from the layer 157. The first layer 151 was then added to complete the stack.

The stacked layers 151–153 and sandwiched needle 154 were placed between two square glass platens each having an edge length of about 3 inches (7.6 cm) and about 0.25 inch (6.4 mm) thick. A weight of about 1.5 pounds (0.68 kg) was added to the upper platen. The weighted stack was placed onto the rack of an industrial oven and heated at 154° C. for a period of approximately 5 hours. The assembly was allowed to cool at room temperature and then the platens were removed. The previously distinct layers 151–153 were permanently bonded around the needle 154 in the resulting device 150. The device 150 appeared translucent in all areas outside of the channel 156 and the needle 154; the channels 156 was cloudy in appearance but still transmitted light.

Following fabrication, electrospray was successfully demonstrated using the device 150. The device 120 was positioned relative to an aluminum plate (not shown) having a hole approximately 2.5 mm in diameter, with the with the distal end of the needle 154 about 3 mm from the mouth of the hole. A DC power supply was then connected, with one terminal each having electrical contact with the plate and with the needle 154. A liquid mixture of 50 parts methanol, 50 parts water, and 1 part acetic acid was delivered to the device (into inlet port 155) at a flow rate of about 10 microliters/minute using an external syringe pump (not shown). A voltage of 2500 volts was applied across the needle and the plate. Droplets of the liquid mixture then formed on the plate opposite the needle 154 in a localized zone of a few centimeters in diameter, demonstrating the efficacy of the electrospray apparatus.

Example 10

Multiple microfluidic devices each having an integral wire for electrically contacting one or more fluid streams was constructed. Referring to FIGS. 8A–8B, a 2.5 inch (6.4 cm) square device 160 was fabricated from five device layers 161–165. The first layer 161 defined four inlet ports 167. The second layer 162 defined four vias 168 aligned with the ports 167. Four channels 171–174 of different widths (5, 10, 20, and 40 mils) (125, 250, 500, and 1000 microns) were defined in the third layer 163 using a computer-controlled plotter modified to manipulate a cutting blade. The fourth and fifth layers 164, 165 were unmodified. Each layer 161–165 was formed of 7.5 mil (188 micron) thickness unoriented "Clear Tear-Seal" polypropylene (American Profol, Cedar Rapids, Iowa). A wire 169 was placed between the second and third layers 162, 163 across the width of the device 160 to contact all four channels 171–174. In a first device 160, the wire 169 was 5 mils (125 microns) in diameter. In a second device 160, the wire 169 was 1 mil (25 microns) in diameter.

Each of the first and the second device 160 were fabricated separately in an identical manner. The layers 161–165 were carefully aligned and stacked together with the wire 169 sandwiched between the second and the third layer 162, 163. The stacked layers 161–165 were placed between two glass platens, and a weight was added to the upper platen to apply a pressure of about 0.26 psi (1.79 kPa). The weighted assembly was placed on a rack in an industrial oven and heated at 154° C. for a period of approximately 5 hours. Following the heating step, the assembly was allowed to cool at room temperature. The previously distinct device layers 161–165 were permanently bonded together, and in the case of both the first and the second device 160, the bond surrounding the wire 169 was sufficiently strong that the wire 169 could not be manually pulled from the device 160. The devices appeared translucent in all areas outside the channels 172–174 and the wire 169; the channels 172–174 assumed a frosty white color but still transmitted light. Notably, in both the first and second devices 160, the 5-mil (125 micron) channel 171 was substantially translucent in appearance and would not pass a flow of pressurized fluid, thus indicating that the channel 171 had collapsed. The first device 160 (having the 5-mil (125 micron) wire) exhibited no noticeable leakage along the intersection between the wire and the second (10 mil (250 micron)) channel. Some leakage was observed in the vicinity of the wire along the intersections with the third and fourth channels 173, 174 in the first device 160. In the second device 160 having a smaller diameter wire, the first channel 171 was collapsed and would not allow passage of any pressurized fluid, but no leakage at all was observed during leak testing of the second, third, and fourth channels 172–174.

As an alternative to using encapsulated wire, polymer device layers patterned with one or more conductive materials such as copper may be used.

Example 11

Adhesiveless microfluidic devices having encapsulated porous membranes (useful as frits) have been constructed. FIGS. 9A–9B provide a representative example of a simple adhesiveless microfluidic channel device 180 having an encapsulated porous frit 185. The device 180 includes four layers 181–184, with the frit placed between the first and second layers 181, 182. The first layer 181 defines two fluidic ports 187, 188. The second layer 182 is identical in appearance to the first layer 181, defining two vias 189, 190 aligned with the ports 187, 188. The third stencil layer 183 defines a channel 191 spanning between the vias 189, 190, the channel 191 defined through the entire thickness of the layer 183. The fourth layer 184 serves to cover and define the lower boundary of the channel 191. The four layer 181–184 may be advantageously formed of unoriented polypropylene, and the frit 185 may be formed of a track-etched polyester membrane such as Poretics PETE Polyester Screen Membrane T01CP02500 (Osmotics Inc., Westborough, Mass.). Frits formed of this material, having a diameter of approximately 0.15 inch (0.38 cm) and a thickness of 0.4 mil (10 micron), have been successfully bonded between 7.5 mil (188 micron) thickness layers of unoriented "Clear Tear-Seal" polypropylene (American Profol, Cedar Rapids, Iowa). Once aligned and stacked together, the device layers 181–185 and frit 185 are preferably placed between glass platens compressed to between about 0.25–0.50 psi (1.72–3.45 kPa), and then heated for a period between 1.5 and 5 hours at a temperature between 154–156° C. Generally, within these ranges, the application of higher pressure and higher temperature within these ranges seem to require shorter heating time to achieve permanent bonding between the layers 181–184.

Example 12

An microfluidic uni-directional valve device having specific unbonded regions may be constructed using adhesiveless bonding methods. In operation, the device has a flexible membrane region that seals against a valve seat to prevent flow in one direction, and that lifts away from the valve seat to allow flow in the other direction. Operation of the adhesiveless device with periodic separation between the flexible region and the valve seat gives rise to the need to prevent permanent bonding along the contact interface during fabrication.

Referring to FIGS. 10A–10B, a microfluidic unidirectional valve device 200 may be fabricated from five device layers 201–205. The first layer 201 serves as a cover. The second layer 202 is a stencil layer defining a channel 206 and interconnected chamber 207 through the entire thickness of the layer 202. The third stencil layer 203 defines a large via 208 and a small aperture 209 penetrating through the layer 203. The third layer 203 is preferably flexible; its flexibility may be enhanced by forming the layer of a thin membrane. The fourth stencil layer 204 defines a via 210 and a channel 211 that opens into a larger chamber 212. Two fluidic ports 214, 216 are defined in the fifth layer 205. The fifth layer 205 (which also serves as a lower cover) is preferably characterized by relatively high rigidity (especially compared to the third layer 203); its rigidity may be enhanced by increasing the thickness of the layer 205. Inserted between the fourth and fifth layers 204, 205 are a valve seat 215 and a degradable spacer element 217 that are aligned with the via 209. The valve seat 215 fits within the chamber 212, and the seat 215 is preferably as least as high (thick) as the fourth layer 204.

The various device layers 201–205 and the valve seat 215 may be advantageously formed from non-oriented polypropylene film, while the degradable spacer element 217 may be formed from materials such as a vinyl film or an acrylic transfer adhesive. The channels 206, 211, chambers 207, 212, vias 208, 210, aperture 209, and ports 214, 216 may be cut through the various layers by means such as a computer-controlled laser cutter or a computer-controlled plotter modified to manipulate a cutting blade. The various layers 201–205, valve seat 215, and spacer element 217 are carefully aligned and then stacked together. Tack welding may be advantageously employed to prevent subsequent slippage between layers. The stacked layers may be placed between glass platens, compressed with an applied pressure between about 0.25–0.50 psi (1.72–3.45 kPa), and then heated for a period, between 1.5 and 5 hours at a temperature between 154–156° C. Generally, within these ranges, the application of higher pressure and higher temperature within these ranges seem to require shorter heating time to achieve permanent bonding between the layers 201–205.

The assembled device 200 is shown in top view FIG. 10B, with a sectional view of a portion of the assembled device shown in FIG. 10C. As shown in FIG. 10C, since the valve seat 215 is preferably at least at thick as the fourth layer 204, addition of the degradable element 217 during assembly locally deforms the third layer 203. Following the heating step, the valve seat 215 is permanently bonded to the fifth layer 205 and the various device layers 201–205 are permanently bonded together. The degradable element 217 may be degraded by exposing it to a chemical solvent such as dichloromethane (DCM). As shown in FIG. 10D, the degradable element may be provided with a central aperture 218 to increase the surface area for interaction with such a solvent. The solvent may be advantageously introduced into both ports 214, 216 of the device 200 to speed the chemical degradation. Following the degradation step, any remnants of the former degradable element 217 may be flushed from the device 200, thus permitting the central layer 203 to contact the valve seat 215 such as shown in FIG. 10E. As an alternative to using a degradable spacer 217, the lower surface of the central layer 203 adjacent to the aperture 209 and/or the upper surface of the valve seat 215 may be coated with an inert substance such as a fluorinated grease or patterned with an inert coating, such as PTFE. Any of these methods will prevent permanent bonding between the third layer 209 and the valve seat 215 during the heating step.

FIGS. 10E–10F are cross-sectional views of a portion of the device 200 in use. In FIG. 10E, fluid is injected through the port 214, and passes through large vias 210, 208 into the channel 206. When the fluid reaches the aperture 209 in the third layer 203, the fluid contacts the valve seat 215. The aperture 209 is smaller than the diameter of the valve seat 215. Accordingly, since the central layer 203 defining the aperture 209 rests upon the valve seat 215, the central layer 203 seals against the valve seat 215 and fluid passage in the direction of the valve seat 215 is blocked. In this particular example, if liquid is used as the working fluid, the liquid may not even reach the valve seat 215, since as it is injected into the device 200, air present within the channel 206, chamber region 207, and large vias 208, 210 may be compressed ahead of the liquid front sufficiently to seal the membrane 203 against the valve seat 215, thus providing a trapped air pocket ahead of the liquid front. An important note is that even drastically increasing the pressure in this example will not cause leakage through the valve, because pressure introduced to the device through the port 214 it simply forces the membrane 203 adjacent to chamber regions 207, 212 into tighter contact against the valve seat.

FIG. 10D provides a second example of operation of the device 200, in which fluid is injected into the other 216. From the inlet port, the fluid passes into the channel segment 211 and the enlarged chamber region 212. In this example, as the fluid pressure is increased, the central layer 203 can be deformed upward into the chamber region 207, since the membrane 203 is constructed from a flexible material. Upward deformation of the membrane 203 opens a flow path that permits fluid in the chamber 212 to flow through the aperture 209, through the chamber 207 and channel 206, and ultimately to the outlet port 214.

Example 13

Twelve adhesiveless microfluidic devices of similar design, each constructed with ten device layers including multiple stencil layers, were fabricated with 7.5 mil (188 micron) thickness adhesiveless, unoriented "Clear Tear-Seal" polypropylene (American Profol, Cedar Rapids, Iowa). Each device defined eight separation channels, and was substantially similar in structure and function to the device 400 illustrated in FIGS. 14A–14B. Each device measured about 3×5.5×0.125 inches (7.6×14×0.32 cm). Various ports, vias, and channels were defined in the device layers using a computer-controlled laser cutter. Each device contained multiple strip-type frit materials (e.g., frits 440, 450, 451) (1-mil/25 microns thickness Celgard 2500 membrane, 55% porosity, 0.209×0.054 micron pore size, Celgard Inc., Charlotte, N.C.) spanning multiple microstructures within the devices. Each of the twelve groups of ten device layers were carefully assembled with the aid of alignment pins to form twelve sub-stacks. No adhesives or bonding agents were used between any of the layers.

An illustration of the apparatus used to bond the twelve microfluidic devices is provided in FIG. 13. A first layer of optical glass (3.75×6×0.5 inches or 9.5×15.2×1.27 cm) was provided to serve as the bottom thermally insulating platen 342 for the stack 340. A second layer of optical glass (3.75×6×0.75 inches or 9.5×15.2×1.91 cm) was provided to serve as the top thermally insulating platen 341 for the stack 340. Thirteen layers of carbon steel foil 343–355 (3×5.5×0.003 inches or 7.6×14×0.008 cm) were provided as spacers to separate the twelve groups of polymeric device layers 361–372 from one another and also from the glass platens 341, 342. Each foil layer had a thermal mass of significantly less than about one-hundredth the thermal mass of either the bottom or top insulating platen 342, 341. The stack 340 was formed with the lower platen 342 on the bottom, followed by a first foil layer 355 substantially centered on the lower platen 342, followed by the first device sub-stack 372, followed by a second foil layer 354, followed by the second device sub-stack 371, followed by a third foil layer 353, and so on, until the twelfth device sub-stack 361 was topped with a thirteenth foil layer 343 and the upper platen 341. The entire stack 340 was placed into a die-cast aluminum enclosure 380 having a removable lid 384. It is believed that enclosing the stack during the heating step in a thermally-conducting enclosure promotes more even temperature distribution when the stack is heated in a conventional industrial (i.e., convection) oven. The enclosure 380 had a wall thickness of about 0.0625 inch (0.159 cm) and an internal volume of about 100 in$^3$ (1640 cm$^3$). The enclosure 380 further had tapped holes 381, 382 along its upper rim adapted to receive threaded bolts 387, 388 to fasten the lid 384. A spring 389 was affixed to the removable lid 384 to compress the stack 340 during the heating step. With the threaded bolts 387, 388 engaging the lid 384 to the enclosure 380, the spring 389 was compressed to provide a force of about 5 lbs (4 N) against the stack 340. Combined with the weight of the upper platen 341, each microfluidic device 361–372 was compressed with a pressure of about 0.37 psi (2.55 kPa).

The enclosure 380 containing the compressed stack 340 was placed into an industrial oven (Blue M Electric Model No. BTN4–100C, Blue M Electric, Williamsport, Pa.) preheated to 152° C. and heated at that temperature for a first heating cycle of about 5 hours. Then, the loaded enclosure 380 was removed from the oven and the lid 384 was removed to expose the upper platen 341. The upper platen 341 was removed, and then a 5-lb (2.3 kg) flat steel block (not shown) at ambient temperature was placed atop the upper foil 343 to speed the cooling process. The open enclosure 380 containing the stacked lower platens 342, foil layers 343–355, device layers 361–372, and steel block was placed on a cooling rack exposed to a forced downward flow of ambient temperature air. The open enclosure 380 and its contents 341–355 and 361–372 were cooled for a period of at least about 30 minutes, after which time the steel block was removed, the upper platen 341 was returned to the stack 340, and the lid 384 was reattached to the enclosure 380 to apply the same compressive force as before to the stack 340. The loaded and sealed enclosure 380 was then placed back into the industrial oven pre-heated to 146° C. and heated for a second heating cycle of about 15 hours. When the second heating cycle was complete, a second cooling cycle identical to the first was initiated. The sealed enclosure 380 was removed from the oven, the lid 384 was removed from the enclosure 380, and the upper platen 341 was removed from the stack 340. A 5-lb (2.3 kg) flat steel block at ambient temperature was placed atop the upper foil 343, and the open enclosure 380 containing the stack 340 (minus the upper platen 341) and the steel block was placed on a cooling rack exposed to a forced downward flow of ambient temperature air. The open enclosure 380 and its contents were cooled to ambient temperature.

Following complete cooling, the stack 340 (minus the upper platen 341) was removed from the enclosure 380 and the thirteen foil layers 343–355 were separated from the polymeric microfluidic devices 361–372. Twelve microfluidic devices 361–372 having uniform, smooth surface finishes and intact microchannel structures formed between permanently bonded layers resulted. No channel collapse or distortion was observed. The devices appeared translucent in all areas not defining microstructures, which themselves appeared slightly cloudy in appearance but still permitted the transmission of light.

Example 14

Six adhesiveless microfluidic high-throughput separation devices each fabricated with twelve device layers and defining twenty-four parallel separation columns, but otherwise similar in design to (and using the same materials as) the device 400 described in connection with FIGS. 14A–14B, were bonded simultaneously. Each of the twenty-four channel devices were larger in area (about 6 inches×8 inches) (about 20.3 cm×15.2 cm) than the eight-column devices described previously. Each group of twelve device layers were placed between thin carbon steel foils (6.375 inches× 8.375 inches×5 mils) (16.2 cm×21.3 cm×125 microns), seven carbon steel foils in total, with two glass platens (5.75 inches×7.75 inches×0.25 inches) (14.6 cm×19.7 cm×0.64 cm) at the outside of the stack. Steel weights (22 lbs/10 kg) were placed atop the upper platen to complete the stack. The entire assembled stack (weight, platens, foils, and groups of device layers) was wrapped in 3 mil thickness aluminum foil, and then placed into a preheated industrial oven (Blue M Electric Model No. BTN4–100C, Blue M Electric, Williamsport, Pa.) set at 153 degrees Celsius. Multiple separate stacks (Applicants have successfully tried up to four stacks) may be placed simultaneously into the industrial oven. A calibrated thermocouple was taped to the top of the weights of one stack. Once a temperature reading of 146 degrees Celsius was obtained from the thermocouple, the stack(s) were heated for six hours and then removed from the oven. The foil was removed, and the hot weights were immediately replaced with identical room-temperature weights. The weighted stacks were then cooled for one hour on a wire rack using a fan, after which point the weights, platens, and foils are removed to yield multiple substantially sealed devices with intact (non-collapsed) channels. The resulting microfluidic separation devices have been used to perform high performance liquid chromatography and operated with internal fluid pressures well in excess of 500 psi (3450 kPa) without leakage or any loss of integrity.

Example 15

In a variant on the previous example (Example 14), each assembled stack (including weights) was wrapped with a few pieces of steel wire to keep the weights in place. The stacks were not wrapped with aluminum foil. Each stack was placed into an industrial oven preheated to 153 degrees Celsius, with up to 4 stacks placed into the oven simultaneously. A thermocouple is taped to the top of at least one stack, and once the reading obtained from the thermocouple reached about 146 degrees C., the condition was maintained for five hours. Each stack was then removed from the oven and the wire was removed from each stack. The hot weights were then replaced with identical room temperature weights. The weighted stacks were then cooled for one hour on a wire rack using a fan, after which point the weights, platens, and foils are removed to yield multiple substantially sealed devices with intact (non-collapsed) channels. As before, these microfluidic separation devices have been used to perform high performance liquid chromatography and operated with internal fluid pressures well in excess of 500 psi (3450 kPa) without leakage or any loss of integrity.

Example 16

In another embodiment, six adhesiveless microfluidic high-throughput separation devices identical to the devices described in connection with Examples 14–15 were bonded. Each group of twelve device layers were placed between thin (5-mil thickness) carbon steel foils, seven carbon steel foils in total, with two glass platens at the outside of the stack. The upper platen measured (5.75 inches×7.75 inches× 0.25 inches) (14.6 cm×19.7 cm×0.64 cm), and the lower platen was the same size except twice as thick. Steel weights (22 lbs/10 kg) were placed atop the upper platen to complete the stack. The entire assembled stack (weight, platens, foils, and groups of device layers) was wrapped in 3 mil thickness aluminum foil, and then placed into a preheated industrial oven (Blue M Electric Model No. BTN4–100C, Blue M Electric, Williamsport, Pa.) set at 153 degrees Celsius for a period of 6.5 hours. Multiple separate stacks (Applicants have successfully tried up to four stacks) may be placed simultaneously into the industrial oven. After heating for 6.5 hours, the foil was removed, and the hot weights were immediately replaced with 27.5 lbs (12.5 kg) of room-temperature weights The weighted stacks were then cooled for a period of 15 minutes on a wire rack using a fan, after which point the weighted stacks were placed back into the oven for an additional heating period of 15 hours at 151 degrees Celsius. The stacks were cooled again by swapping room temperature weights 27.5 lbs (12.5 kg) for the hot weights, and then cooling for one hour on a wire rack in a flow of fan-forced room-temperature air. Thus, the heating step included portions at two different temperatures and two different pressures. Thereafter, the weights, platens, and foils are removed to yield multiple substantially sealed devices with intact (non-collapsed) channels. The resulting microfluidic separation devices have been used to perform high performance liquid chromatography and operated with internal fluid pressures well in excess of 500 psi (3450 kPa) without leakage or any loss of integrity.

Although embodiments of the present invention has been described in detail by way of illustration and example to promote clarity and understanding, it will be apparent that certain changes and modifications may be practiced within the scope of the appended claims.

What is claimed is:

1. A method for fabricating a microfluidic device, the method comprising the steps of:
    providing a first substantially flat platen and a second substantially flat platen;
    providing a plurality of substantially planar, substantially metal-free, adhesiveless polymer device layers including:
        a first cover layer and a second cover layer, at least one of the first cover layer and the second cover layer defining a fluidic port; and
        at least one stencil layer defining a microfluidic channel penetrating through the entire thickness of the at least one stencil layer, the microfluidic channel being bounded laterally by the at least one stencil layer, and being bounded from above and below by additional device layers of the plurality of device layers to define an upper channel surface and a lower channel surface;
    stacking the plurality of device layers between the first platen and the second platen; and
    controllably heating the plurality of stacked device layers according to a heating profile adapted to form a substantially sealed adhesiveless microfluidic device wherein the upper channel surface remains distinct from the lower channel surface.

2. The method of claim 1, further comprising the step of applying a compressive force to the plurality of stacked device layers during at least a portion of the heating step.

3. The method of claim 2 wherein the compressive force is less than about 10 psi.

4. The method of claim 2 wherein the compressive force is less than about 2 psi.

5. The method of claim 2 wherein one or more weights are used in conjunction with at least one of the first platen and the second platen to apply the compressive force.

6. The method of claim 2 wherein the compressive force is controllably varied during at least a portion of the heating step.

7. The method of claim 1, further comprising the step of sensing the temperature of at least one of the first platen, the second platen, and any device layer of the plurality of device layers, wherein the heating step is responsive to the sensing step.

8. The method of claim 1, further comprising the step of cooling the plurality of device layers following the heating step.

9. The method of claim 8 wherein a compressive force is applied to the platens during the cooling step.

10. The method of claim 8, further comprising the step of sensing the temperature of at least one of the first platen, the second platen, and any device layer of the plurality of device layers, wherein the cooling step is responsive to the sensing step.

11. The method of claim 1 wherein the controllable heating step includes a first heating sub-step, a cooling sub-step, and a second heating sub-step.

12. The method of claim 11 wherein the first heating sub-step heats the plurality of stacked device layers to a first temperature, the second heating sub-step heats the plurality of stacked device layers to a second temperature, and the second temperature is lower than the first temperature.

13. The method of claim 1, further comprising the step of drying the plurality of device layers prior to the heating step.

14. The method of claim 1, further comprising the step of drying the plurality of device layers during at least a portion of the heating step.

15. The method of claim 1, wherein the controllable heating of the plurality of device layers is performed by heating the platens.

16. The method of claim 15 wherein the platens are heated from a process selected from the group consisting of: thermoelectric heating, resistive heating, convective heating, and conductive heating.

17. The method of claim 8, wherein the controllable cooling of the plurality of device layers is performed by cooling at least one of the first platen and the second platen.

18. The method of claim 1, wherein the heating step includes heating the plurality of device layers to within ±10 percent of the Celsius differential scanning calorimetric melting point of the polymer.

19. The method of claim 1, wherein the heating step includes heating the plurality of device layers to within ±5 percent of the Celsius differential scanning calorimetric melting point of the polymer.

20. The method of claim 1, wherein the heating step includes heating the plurality of device layers to within ±2 percent of the Celsius differential scanning calorimetric melting point of the polymer.

21. The method of claim 1 wherein the polymer comprises a polyolefin material.

22. The method of claim 1, further comprising the step of enclosing the plurality of stacked device layers and platens in a substantially sealed enclosure during the heating step.

23. The method of claim 1 wherein the first platen and the second platen are thermally insulating, the method further comprising the steps of:
    providing a first thin thermally conducting layer and a second thin thermally conducting layer; and
    prior to the heating step, stacking the first thin thermally conducting layer between the first platen and the plurality of device layers, and stacking the second thin thermally conducting layer between the second platen and the plurality of device layers.

24. The method of claim 23 wherein the platens are fabricated with glass.

25. The method of claim 23 wherein the thermally conducting layers comprise at least one material selected from the group consisting of: carbon steel, stainless steel, aluminum, and copper.

26. The method of claim 1, further comprising the step of placing a degradable material between two or more device layers of the plurality of device layers in one or more specific regions prior to the heating step to prevent permanent bonding between the two or more device layers in the one or more specific regions.

27. The method of claim 26, further comprising the steps of:
    degrading the degradable material; and
    removing the degraded material from the substantially sealed microstructure through the fluidic port.

28. The method of claim 27 wherein the degrading step includes chemical degradation, and the removing step includes flushing with a fluid.

29. The method of claim 1, further comprising the step of patterning a coating on at least one selected region of at least one device layer of the plurality of device layers to prevent permanent bonding between adjacent device layers in the at least one selected region.

30. A microfluidic device having a plurality of microfluidic channels defined in different stencil layers, the device fabricated according to the method of claim 1.

31. An adhesiveless microfluidic device comprising a plurality of substantially planar device layers including:
- a first cover layer and a second cover layer, with at least one cover layer defining a fluidic port; and
- at least one stencil layer disposed between the first cover layer and the second cover layer, the at least one stencil defining a microfluidic channel through the entire thickness of the at least one stencil layer, the channel being bounded from above and below by additional device layers of the plurality of device layers to define an upper channel surface and a lower channel surface, and the channel being in fluid communication with the fluidic port;

wherein the first cover layer, second cover layer, and the at least one stencil layer are fabricated with substantially metal-free, adhesiveless polymer materials, and the layers are interpenetrably bound together to form a substantially sealed adhesiveless microstructure with the upper surface remaining distinct from the lower surface.

32. The device of claim 31 wherein the resulting microfluidic device remains substantially sealed with an internal fluid pressure of at least about 100 psi.

33. The method of claim 31 wherein the resulting microfluidic device remains substantially sealed with an internal fluid pressure of at least about 500 psi.

34. The microfluidic device of claim 31 wherein the device layers are substantially colorless.

35. The microfluidic device of claim 31 wherein the device layers are unoriented polymers.

36. The microfluidic device of claim 31 wherein the device layers are fabricated with polyolefin materials.

37. The method of claim 31 wherein the at least one stencil layer has a thickness of less than or equal to about 250 microns.

38. The microfluidic device of claim 31, further comprising at least one electrical conductor sealingly engaged between at least two device layers of the plurality of device layers to provide an electrically conductive path into or out of the microstructure.

39. The microfluidic device of claim 38 wherein the at least one electrical conductor is used to promote fluid movement within the microstructure.

40. The microfluidic device of claim 31, further comprising a hollow electrospray needle disposed at least partially within the microstructure.

41. The microfluidic device of claim 31, further comprising a capillary tube disposed at least partially within the microstructure.

42. The microfluidic device of claim 31, further comprising at least one sensor permitting sensory communication with the microstructure.

43. The microfluidic device of claim 31, further comprising a porous membrane disposed between at least two device layers of the plurality of device layers, the porous membrane being in fluid communication with the microstructure.

44. The microfluidic device of claim 43 wherein the porous membrane is substantially smaller than the plurality of device layers.

45. A method for fabricating a plurality of microfluidic devices simultaneously, the method comprising the steps of:
- providing a first substantially flat, thermally insulating platen and a second substantially flat, thermally insulating platen;
- providing a plurality of thin thermally conducting layers;
- providing a plurality of groups of substantially planar, substantially metal-free, adhesiveless polymer device layers, each group including at least one stencil layer defining a microfluidic channel penetrating through the entire thickness of the at least one stencil layer, the microfluidic channel being bounded laterally by the at least one stencil layer, and being bounded from above and below by additional device layers of the plurality of device layers within the same group to define an upper channel surface and a lower channel surface;
- stacking the plurality of groups of device layers, the plurality of thermally conducting layers, the first platen, and the second platen with the first platen and the second platen on the outside, and with each group of polymer layers disposed between two thermally conducting layers of the plurality of thermally conducting layers; and
- controllably heating the plurality of groups of device layers according to a heating profile adapted to bond each group of device layers into a substantially sealed microfluidic device wherein the upper channel surface remains distinct from the lower channel surface.

46. The method of claim 45, further comprising the step of applying a compressive force to the plurality of groups of stacked device layers during at least a portion of the heating step.

47. The method of claim 46 wherein the compressive force is less than about 10 psi.

48. The method of claim 46 wherein the compressive force is less than about 2 psi.

49. The method of claim 46 wherein one or more weights are used in conjunction with at least one of the first platen and the second platen to apply the compressive force.

50. The method of claim 45, further comprising the step of sensing the temperature of at least one of the first platen, the second platen, and any device layer of the plurality of device layers, wherein the heating step is responsive to the sensing step.

51. The method of claim 45, further comprising the step of cooling the plurality of groups of device layers following the heating step, wherein a compressive force is applied to the plurality of groups of device layers during the cooling step.

52. The method of claim 45 wherein the controllable heating step includes a first heating sub-step, a cooling sub-step, and a second heating sub-step.

53. The method of claim 52 wherein the first heating sub-step heats the plurality of groups of device layers to a first temperature, the second heating sub-step heats the plurality of groups of device layers to a second temperature, and the second temperature is lower than the first temperature.

54. The method of claim 45, further comprising the step of drying the plurality of groups of device layers prior to the heating step.

55. The method of claim 45, further comprising the step of drying the plurality of groups of device layers during at least a portion of the heating step.

56. The method of claim 45, wherein the heating step includes heating the plurality of device layers to within ±10 percent of the Celsius differential scanning calorimetric melting point of the polymer.

57. The method of claim 45, wherein the heating step includes heating the plurality of groups of device layers to within ±5 percent of the Celsius differential scanning calorimetric melting point of the polymer.

58. The method of claim 45, wherein the heating step includes heating the plurality of groups of device layers to within ±2 percent of the Celsius differential scanning calorimetric melting point of the polymer.

59. The method of claim 45, further comprising the step of enclosing the plurality of groups of device layers, conducting layers, and platens in a substantially sealed enclosure during the heating step.

60. The method of claim 45 wherein the plurality of groups of device layers comprise polyolefin materials.

61. The method of claim 45 wherein the first platen and the second platen are fabricated with glass.

62. The method of claim 45 wherein the thermally conducting layers comprise at least one metal selected from the group consisting of: carbon steel, stainless steel, aluminum, and copper.

* * * * *